(12) United States Patent
Bono et al.

(10) Patent No.: US 7,294,628 B2
(45) Date of Patent: Nov. 13, 2007

(54) PIPERAZINYLACYLPIPERIDINE DERIVATIVES, THEIR PREPARATION AND THERAPEUTIC USE THEREOF

(75) Inventors: Françoise Bono, Toulouse (FR); Michaël Bosch, Marsillargues (FR); Victor Dos Santos, Valergues (FR); Jean-Marc Herbert, Tourneefuille (FR); Dino Nisato, Saint-Georges d'Orques (FR); Bernard Tonnerre, Vailhauques (FR); Jean Wagnon, Montpellier (FR)

(73) Assignee: Sanofi-Aventis, Paris (FR)

( * ) Notice: Subject to any disclaimer, the term of this patent is extended or adjusted under 35 U.S.C. 154(b) by 453 days.

(21) Appl. No.: 10/516,808

(22) PCT Filed: Jun. 5, 2003

(86) PCT No.: PCT/FR03/01686

§ 371 (c)(1),
(2), (4) Date: Dec. 3, 2004

(87) PCT Pub. No.: WO03/104226

PCT Pub. Date: Dec. 18, 2003

(65) Prior Publication Data

US 2006/0167007 A1  Jul. 27, 2006

(30) Foreign Application Priority Data

Jun. 7, 2002  (FR) ................................. 02 07001

(51) Int. Cl.
*A61K 31/497* (2006.01)
*A61K 31/4965* (2006.01)
*C07D 241/04* (2006.01)
*C07D 295/00* (2006.01)

(52) U.S. Cl. .......................... 514/252.13; 514/255.01; 514/255.05; 544/358; 544/360; 544/367; 544/372; 544/374; 544/386

(58) Field of Classification Search ............... None
See application file for complete search history.

(56) References Cited

U.S. PATENT DOCUMENTS 4,994,455 A * 2/1991 Welch, Jr. ................ 514/216
2003/0083347 A1 5/2003 Baroni et al.

FOREIGN PATENT DOCUMENTS

FR  2 803 593 A  7/2001

WO  WO 00 69829  11/2000

OTHER PUBLICATIONS

West, Anthony R., Solid State Chemistry and Its Applications, Wiley, New York, 1988, 358.*
Venters, H.D., et al., Tumor Necrosis Factor-α Induces Neuronal Death by Silencing Survival Signals Generated by the Type I Insulin-like Growth Factor Receptor, Annals New York Academy of Sciences, 917(1) 210-220 (2000).*

* cited by examiner

*Primary Examiner*—James O. Wilson
*Assistant Examiner*—Erich Leeser
(74) *Attorney, Agent, or Firm*—Balaram Gupta

(57) ABSTRACT

The invention relates to substituted 1-piperazinylacylpiperidine derivatives of general formula (I)

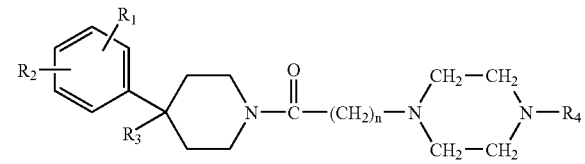

(I)

in which:
n is 1 or 2;
$R_1$ represents a halogen atom; a trifluoromethyl radical; a $(C_1-C_4)$ alkyl; a $(C_1-C_4)$alkoxy; a trifluoromethoxy radical;
$R_2$ represents a hydrogen atom or a halogen atom;
$R_3$ represents a hydrogen atom; a group —$OR_5$; a group —$CH_2OR_5$; a group —$NR_6R_7$; a group —$NR_8COR_9$; a group —$NR_8CONR_{10}R_{11}$; a group —$CH_2NR_{12}R_{13}$; a group —$CH_2NR_8CONR_{14}R_{15}$; a $(C_1-C_4)$alkoxycarbonyl; a group —$CONR_{16}R_{17}$;
or else $R_3$ constitutes a double bond between the carbon atom to which it is attached and the adjacent carbon atom of the piperidine ring;
$R_4$ represents the aromatic group 1,3-thiazol-2-yl of formula:

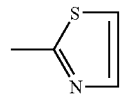

Preparation process and therapeutic application.

10 Claims, No Drawings

PIPERAZINYLACYLPIPERIDINE DERIVATIVES, THEIR PREPARATION AND THERAPEUTIC USE THEREOF

The present invention relates to substituted 1-piperazinylacylpiperidine derivatives, their preparation and their therapeutic application.

The compounds according to the present invention exhibit affinity for the neurotrophin receptor $p75^{NTR}$.

Neurotrophins belong to a family of proteins which possess a similar structure and similar functions and include nerve growth factor (NGF), BDNF (Brain Derived Neurotrophic Factor), neurotrophin-3 (NT-3), neurotrophin-4/5 (NT-4/5) and neurotrophin-6 (NT-6). The biological effects of these proteins (survival and differentiation) are exerted through interaction with membrane receptors having tyrosine kinase activity (trk-A, trk-B and trk-C) (H. THOENEN, Science, 1995, 270, 593-598; G. R. LEWIN and Y. A. BARDE, Annu. Rev. Neurosci., 1996, 19, 289-317; M. V. CHAO, J., Neurobiol., 1994, 25, 1373-1385; M. BOTHWELL, Annu. Rev. Neurosci., 1995, 18, 223-253; G. DECHANT and Y. A. BARDE, Curr. Opin. Neurobiol., 1997, 7, 413-418). However, many studies show the preponderant role of the $p75^{NTR}$ receptor in the activity of neurotrophins.

The $p75^{NTR}$ receptor, the receptor for all neurotrophins, is a transmembrane glycoprotein of the tumour necrosis factor (TNF) receptor family (W. J. FRIEDMAN and L. A. GREENE, Exp. Cell. Res., 1999, 253, 131-142; J. MELDOSIS et al., Trends Pharmacol. Sci., 2000, 21, 242-243). A number of biological functions are attributed to the $p75^{NTR}$ receptor: on the one hand, the modulation of the affinity of neurotrophins for trk receptors; on the other hand, in the absence of trk, induction of a signal for cell death by apoptosis which occurs through homodimerization of the receptor and activation of the ceramide pathway.

Apoptosis, or programmed cell death, is a physiological mechanism for elimination of cells in numerous tissues. In particular, apoptosis plays a preponderant role in embryogenesis, morphogenesis and cell renewal. Apoptosis is a genetically controlled phenomenon which only occurs at an advanced and irreversible stage of cell lesion.

Many studies show that apoptosis occurs in several pathologies of the central nervous system such as amyotrophic lateral sclerosis, multiple sclerosis, Alzheimer's, Parkinson's and Huntington's diseases and prion diseases. Furthermore, neuronal death through apoptosis also occurs very early after cerebral and cardiac ischaemia. Cell death is also a preponderant phenomenon in atherosclerosis; indeed, the necrosis zones in primary atherosclerotic lesions in humans are evaluated at 80% (M. L. BOCHATON-PIALAT et al., Am. J. Pathol., 1995, 146, 1-6; H. PERLMAN, Circulation, 1997, 95, 981-987). Apoptosis is also involved in mechanisms leading to cell death following cardiac ischaemia-reperfusion (H. YAOITA et al., Cardiovasc. Res., 2000, 45, 630-641).

Several studies show that the $p75^{NTR}$-dependent pro-apoptotic signal is observed in various cell types including neuronal cells, oligodendrocytes, Schwann cells and also hepatic, cardiac and smooth muscle cells (J. M. FRADE et al., Nature, 1996, 383, 166-168; P. LASACCIA-BONNEFIL et al., Nature, 1996, 383, 716-719; M. SOILU-HANNINEN et al., J. Neurosci., 1999, 19, 4828-4838; N. TRIM et al., Am. J. Pathol., 2000, 156, 1235-1243; S. Y. WANG et al., Am. J. Pathol., 2000, 157, 1247-1258). Moreover, a number of experiments carried out in vivo show an increase in the expression of $p75^{NTR}$ following ischaemia in regions of the brain and of the heart in which massive apoptosis is recorded. These results therefore suggest that $p75^{NTR}$ may play a preponderant role in the mechanisms leading to neuronal death through apoptosis post ischaemia (P. P. ROUX et al., J. Neurosci., 1999, 19, 6887-6896; J. A. PARK et al., J. Neurosci., 2000, 20, 9096-9103).

The $p75^{NTR}$ receptor is described as a cellular target for the prion peptide (V. DELLA-BIANCA et al., J. Biol. Chem., 2001, in press) and for the β-amyloid peptide (S. RABIZADEH et al., Proc. Natl. Acad. Sci. USA, 1994, 91, 10703-10706) and would thus be involved in apoptotic phenomena induced by these compounds. These results support the hypothesis according to which $p75^{NTR}$ would play an important role in neuronal death induced by the infectious prion protein (transmissible spongiform encephalopathy) or by the beta-amyloid protein (Alzheimer's disease).

Recent studies suggest that the $p75^{NTR}$ receptor might also play an important role in axonal regeneration, via its function as co-receptor for the Nogo receptor (WONG et al., Nature Neurosci., 2002, 5, 1302-1308; Kerracher and Winton, Neuron, 2002, 36, 345-348). Indeed, several myelin-associated proteins (myelin-associated glycoprotein, MAG, Nogo-A and oligodendrocyte myelin glycoprotein OMgp) inhibit nerve regeneration at the central level during medullary or cranial trauma. These proteins are located in the membrane of the oligodendrocytes directly adjacent to the axon and inhibit neuritic growth by binding with a high affinity to the Nogo receptor located on the axonal membrane. The $p75^{NTR}$ receptor is associated with the Nogo receptor and is involved in the signalling of the inhibitory effects of these myelin proteins in relation to axonal growth. As a result, the $p75^{NTR}$ receptor plays a major role in the regulation of neuronal plasticity and in neuron-glia interactions and represents a therapeutic target of choice for promoting nerve regeneration.

At the peripheral level, recent studies show an increase in the expression of $p75^{NTR}$ and of neurotrophins and a massive apoptosis in atherosclerotic lesions. Furthermore, a proangiogenic and vasodilative effect of NGF is also recorded. Finally, a novel form of $p75^{NTR}$ which is truncated in the extracellular part has been identified as well as its major role in established vasculogenesis (D. VON SHACK et al., Nature Neuroscience, 2001, 4, 977-978). All these recent data suggest that $p75^{NTR}$ in its whole or truncated form could also play a preponderant role in vascular pathologies.

A number of compounds are known to interact with the trkA/NGF/$p75^{NTR}$ system or to possess an NGF-type activity. Thus, patent application WO 00/59893 describes substituted pyrimidine derivatives which demonstrate an NGF-type activity and/or which increase the activity of NGF on PC12 cells. Patent applications WO 00/69828 and WO 00/69829 describe polycyclic compounds which inhibit the binding of NGF to the $p75^{NTR}$ receptor in cells which do not express the trkA receptor. Application WO 94/11373 describes pyridazinoquinazolone derivatives which bind to the neurotrophin receptor $p75^{NTR}$. Application WO 94/22866 describes pyrazoloquinazolone derivatives which specifically bind to NGF so as to avoid its attachment to the $p75^{NTR}$ receptor but allowing it to interact with the trk receptor. Application WO 01/49684 describes substituted tetrahydropyridine derivatives which possess activity vis-à-vis the modulation of TNF-alpha.

New 1-piperazinylacylpiperidine derivatives have now been found which exhibit affinity for the receptor $p75^{NTR}$.

The present invention provides compounds of the formula (I):

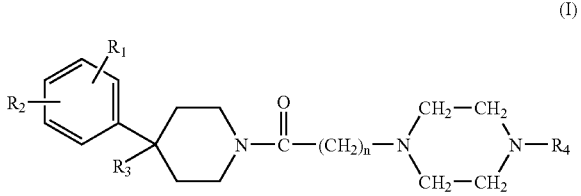

(I)

in which:

n is 1 or 2;

$R_1$ represents a halogen atom; a trifluoromethyl radical; a $(C_1-C_4)$alkyl; a $(C_1-C_4)$alkoxy; a trifluoromethoxy radical;

$R_2$ represents a hydrogen atom or a halogen atom;

$R_3$ represents a hydrogen atom; a group —$OR_5$; a group —$CH_2OR_5$; a group —$NR_6R_7$; a group —$NR_8COR_9$; a group —$NR_8CONR_{10}R_{11}$; a group —$CH_2NR_{12}R_{13}$; a group —$CH_2NR_8CONR_{14}R_{15}$; a $(C_1-C_4)$alkoxycarbonyl; a group —$CONR_{16}R_{17}$;

or else $R_3$ constitutes a double bond between the carbon atom to which it is attached and the adjacent carbon atom of the piperidine ring;

$R_4$ represents the aromatic group 1,3-thiazol-2-yl of formula:

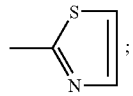

$R_5$ represents a hydrogen atom; a $(C_1-C_4)$alkyl; a $(C_1-C_4)$alkylcarbonyl;

$R_6$ and $R_7$ represent each independently a hydrogen atom or a $(C_1-C4)$ alkyl;

$R_8$ represents a hydrogen atom or a $(C_1-C_4)$alkyl;

$R_9$ represents a $(C_1-C_4)$alkyl or a group —$(CH_2)_m$—$NR_6R_7$;

m is 1, 2 or 3;

$R_{10}$ and $R_{11}$ represent each independently a hydrogen atom or a $(C_1-C_4)$alkyl;

$R_{12}$ and $R_{13}$ represent each independently a hydrogen atom or a $(C_1-C_5)$alkyl; $R_{13}$ may also represent a group —$(CH_2)_q$—OH or a group —$(CH_2)_q$—S—$CH_3$;

or else $R_{12}$ and $R_{13}$, together with the nitrogen atom to which they are attached, constitute a heterocycle selected from aziridine, azetidine, pyrrolidine, piperidine and morpholine;

q is 2 or 3;

$R_{14}$ and $R_{15}$ represent each independently a hydrogen atom or a $(C_1-C_4)$alkyl;

$R_{16}$ and $R_{17}$ represent each independently a hydrogen atom or a $(C_1-C_4)$alkyl; $R_{17}$ may also represent a group —$(CH_2)_q$—$NR_6R_7$;

or else $R_{16}$ and $R_{17}$, together with the nitrogen atom to which they are attached, constitute a heterocycle selected from azetidine, pyrrolidine, piperidine, morpholine and piperazine which is unsubstituted or substituted in position 4 by a $(C_1-C_4)$alkyl.

The compounds of formula (I) may exist in the form of bases or addition salts with acids. Such addition salts form part of the invention.

These salts are advantageously prepared with pharmaceutically acceptable acids, although the salts of other acids useful for the purification or isolation of compounds of formula (I) also form part of the invention.

The compounds of formula (I) may also exist in the form of hydrates or solvates, specifically in the form of associations or combinations with one or more molecules of water or with a solvent. Such hydrates and solvates also form part of the invention.

A halogen atom is an atom of bromine, chlorine, fluorine or iodine.

$(C_1-C_4)$Alkyl or $(C_1-C_5)$alkyl respectively is a linear or branched alkyl radical of one to four carbon atoms or one to five carbon atoms, respectively, such as the methyl, ethyl, propyl, isopropyl, butyl, isobutyl, sec-butyl, tert-butyl, pentyl, isopentyl, neopentyl or tert-pentyl radical.

$(C_1-C_4)$Alkoxy is a linear or branched alkoxy radical of one to four carbon atoms, such as the methoxy, ethoxy, propoxy, isopropoxy, butoxy, isobutoxy, sec-butoxy or tert-butoxy radical.

Particular preference is given to the compounds of formula (I) wherein:

n is 1;

$R_1$ is in position 3 of the phenyl and represents a trifluoromethyl radical, a methyl, a methoxy or a trifluoromethoxy radical and $R_2$ represents a hydrogen atom; or else $R_1$ is in position 3 of the phenyl and represents a trifluoromethyl radical and $R_2$ is in position 4 of the phenyl and represents a chlorine atom;

$R_3$ represents a hydroxyl, a methoxy, an aminomethyl, a (methylamino)methyl, a (dimethylamino)methyl; or else $R_3$ constitutes a double bond between the double bond between the carbon atom to which it is attached and the adjacent carbon atom of the piperidine ring;

$R_4$ represents a 1,3-thiazol-2-yl;

in the form of a base or an addition salt with an acid, and also in the form of a hydrate or solvate.

Among the compounds of formula (I) provided by the invention particular mention may be made of the following compounds:

1-[4-hydroxy-4-[3-(trifluoromethyl)phenyl]-1-piperidyl]-2-[4-(1,3-thiazol-2-yl)-1-piperazinyl]-1-ethanone;

2-[4-(1,3-thiazol-2-yl)-1-piperazinyl]-1-[4-[3-(trifluoromethyl)phenyl]-3,6-dihydro-1-(2H)-pyridinyl]-1-ethanone;

1-[4-(aminomethyl)-4-[3-(trifluoromethyl)phenyl]-1-piperidyl]-2-[4-(1,3-thiazol-2-yl)-1-piperazinyl]-1-ethanone;

1-[4-[4-chloro-3-(trifluoromethyl)phenyl]-4-hydroxy-1-piperidyl]-2-[4-(1,3-thiazol-2-yl)-1-piperazinyl]-1-ethanone;

1-[4-hydroxy-4-(3-methoxyphenyl)-1-piperidyl]-2-[4-(1,3-thiazol-2-yl)-1-piperazinyl]-1-ethanone;

1-[4-hydroxy-4-(3-methylphenyl-1-piperidyl]-2-[4-(1,3-thiazol-2-yl)-1-piperazinyl]-1-ethanone;

1-[4-methoxy-4-[3-(trifluoromethyl)phenyl]-1-piperidyl]-2-[4-(1,3,-thiazol-2-yl)-1-piperazinyl]-1-ethanone;

1-[4-hydroxy-4-[3-(trifluoromethoxy)phenyl]-1-piperidyl]-2-[4-(1,3-thiazol-2-yl)-1-piperazinyl]-1-ethanone;

1-[4-[(dimethylamino)methyl]-4-[3-(trifluoromethyl)phenyl]-1-piperidyl]-2-[4-(1,3-thiazol-2-yl)-1-piperazinyl]-1-ethanone;

1-[4-[(methylamino)methyl]-4-[3-(trifluoromethyl)phenyl]-1-piperidyl]-2-[4-(1,3-thiazol-2-yl)-1-piperazinyl]-1-ethanone;

in the form of base or an addition salt of an acid, and in the form of a hydrate or solvate.

In another of its aspects the present invention provides a process for preparing compounds of formula (I) in which n=1, characterized in that:

a1) a compound of the formula

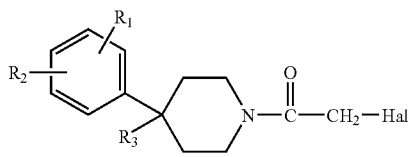

in which $R_1$, $R_2$ and $R_3$ are as defined for a compound of formula (I) and Hal represents a halogen atom, preferably chlorine or bromine, with the proviso that when $R_3$ contains a hydroxyl or amine function these functions can be protected, is reacted with a compound of formula

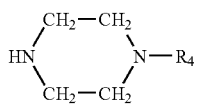

in which $R_4$ is as defined for a compound of formula (I);

b1) and, following deprotection where appropriate of the hydroxyl or amine functions present in $R_3$, the compound of formula (I) is obtained.

Where appropriate, the compound of formula (I) is converted into one of its addition salts with an acid.

In another of its aspects the present invention provides a process for preparing compounds of formula (I) in which n=2, characterized in that:

a2) a compound of formula

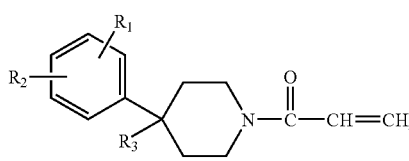

in which $R_1$, $R_2$ and $R_3$ are as defined for a compound of formula (I), with the proviso that when $R_3$ contains a hydroxyl or amine function these functions can be protected, is reacted with a compound of formula

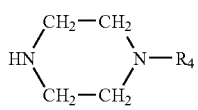

in which $R_4$ is as defined for a compound of formula (I);

b2) and, following deprotection where appropriate of the hydroxyl or amine functions present in $R_3$, the compound of formula (I) is obtained.

Where appropriate, the compound of formula (I) is converted into one of its addition salts with an acid.

In step a1) or in step a2), when a compound of formula (IIa) or (IIb) is reacted with a compound of formula (III), the reaction is carried out in the presence of a base selected from organic bases such as triethylamine, N,N-diisopropylethylamine or N-methylmorpholine or from alkali metal carbonates or bicarbonates such as potassium carbonate, sodium carbonate or sodium bicarbonate and in the absence or presence of an alkali metal iodide such as potassium iodide or sodium iodide. The reaction is carried out in a solvent such as acetonitrile, N,N-dimethylformamide, toluene or propan-2-ol and at a temperature between the ambient temperature and the reflux temperature of the solvent.

Where appropriate, in step b1) or in step b2), the hydroxyl or amine functions present in $R_3$ are deprotected in accordance with the conventional methods well known to the person skilled in the art.

In one version of the process and when $R_3$ represents a group $-CH_2NR_{12}R_{13}$ in which $R_{12}$ and $R_{13}$ each represent hydrogen a3) a compound of formula

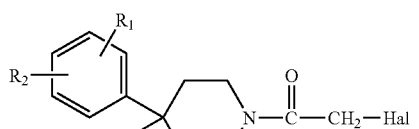

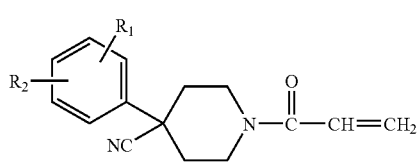

in which $R_1$, $R_2$ and $R_3$ are as defined for a compound of formula (I) and Hal represents a halogen atom, preferably chlorine or bromine, is reacted with a compound of formula

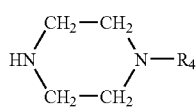

in which $R_4$ is as defined for a compound of formula (I), to give a compound of formula

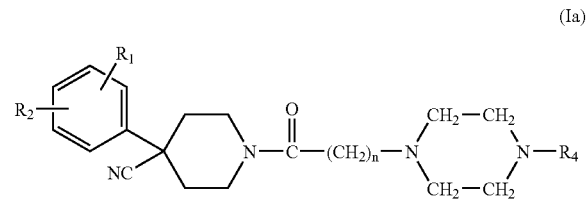

b3) the cyano group of the compound of formula (Ia) is reduced to give a compound of formula (I) in which $R_3=CH_2NH_2$.

Where appropriate the compound of formula (I) is converted into one of its addition salts with an acid.

In step a3) the reaction between the compound of formula (IIc) or (IId) and the compound of formula (III) is carried out as described above in step a1) or a2) of the process according to the invention.

In step b3) the reduction of the cyano group of the compound of formula (Ia) is carried out in accordance with conventional methods. Thus, for example, the reduction is carried out by hydrogenation in the presence of a catalyst such as Raney® nickel or rhodium on alumina and in the presence or absence of ammonia in a solvent such as methanol, N,N-dimethylformamide or tetrahydrofuran or a mixture of these solvents and at a temperature between ambient temperature and 60° C.

In another version of the process and when $R_3$ constitutes a double bond between the carbon atom to which it is attached and the adjacent carbon atom of the piperidine ring a compound of formula

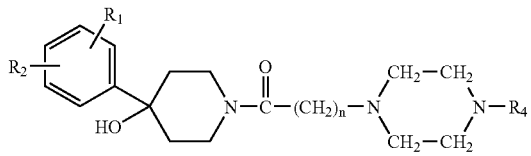

$R_3 = $ —OH in which $R_1$, $R_2$, n and $R_4$ are as defined for a compound of formula (I) is dehydrated to give a compound of formula

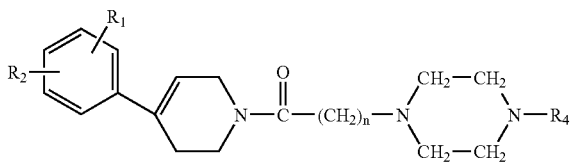

Where appropriate the compound of formula (I) is converted into one of its addition salts with an acid.

The dehydration is carried out using for example an acetic acid/hydrochloric acid mixture or an acetic acid/sulphuric acid mixture at a temperature between the ambient temperature and 140° C. The reaction can also be carried out using p-toluenesulphonic acid, in a solvent such as toluene and at a temperature between the ambient temperature and the reflux temperature.

A compound of formula (I) in which $R_3$ represents a group —$CH_2NR_{12}R_{13}$ in which $R_{12}$=H and $R_{13}$=($C_1$-$C_5$)alkyl may also be prepared by reacting a compound of formula (I) in which $R_3$=—$CH_2NH_2$ with a ($C_1$-$C_5$)alkyl halide in the presence of a base such as an alkali metal carbonate such as potassium carbonate in a solvent such as acetonitrile, N,N-dimethylformamide or tetrahydrofuran at a temperature between the ambient temperature and the reflux temperature of the solvent. An identical reaction is used to prepare the compounds of formula (I) in which $R_{12}$ et $R_{13}$ each represent the same or a different ($C_1$-$C_5$)alkyl.

A compound of formula (I) in which $R_3$ represents a group —$CH_2NR_{12}R_{13}$ in which $R_{12}$=H or ($C_1$-$C_5$)alkyl and $R_{13}$=($C_1$-$C_5$)alkyl, a group —$(CH_2)_q$—OH or a group —$(CH_2)_q$—S—$CH_3$ respectively may also be prepared by reacting a compound of formula (I) in which $R_3$=—$CH_2$—$NHR_{12}$ with formaldehyde or with an aldehyde of formula OHC—($C_1$-$C_4$)alkyl, OHC—$(CH_2)_{q-1}$—OH or OHC—$(CH_2)_{q-1}$—S—$CH_3$ respectively, or with a corresponding ketone, in the presence of a reducing agent such as sodium borohydride or sodium triacetoxyborohydride and in the presence of an acid such as acetic acid in a solvent such as dichloromethane or tetrahydrofuran at a temperature between 0° C. and the ambient temperature.

A compound of formula (I) in which $R_3$ represents a group —$CH_2NR_{12}R_{13}$ in which $R_{12}$ et $R_{13}$, together with the nitrogen atom to which they are attached, constitute aziridine may also be prepared by cyclizing a corresponding intermediate in which $R_3$ represents a group —$CH_2NH$—$CH_2CH_2$—Cl in the presence of a base such as an alkali metal carbonate such as potassium carbonate and in the presence of an alkali metal iodide such as potassium iodide in a solvent such as acetonitrile and at a temperature between the ambient temperature and the reflux temperature of the solvent; the corresponding intermediate is prepared by reacting a compound of formula (I) in which $R_3$=—$CH_2NH_2$ with chloroacetaldehyde by the method described above.

A compound of formula (I) in which $R_3$ represents a group —$CH_2NR_{12}R_{13}$ in which $R_{12}$ and $R_{13}$, together with the nitrogen atom to which they are attached, constitute azetidine, pyrrolidine, piperidine or morpholine, respectively, may also be prepared by reacting a compound of formula (I) in which $R_3$=—$CH_2NH_2$ with a compound of formula Hal-$(CH_2)_3$-Hal, Hal-$(CH_2)_4$-Hal, Hal-$(CH_2)_5$-Hal or Hal-$CH_2CH_2$—O—$CH_2CH_2$-Hal respectively, in which Hal represents a halogen atom, preferably chlorine or bromine, in the presence of a base such as an alkali metal carbonate such as potassium carbonate or in the presence of an alkali metal iodide such as potassium iodide in a solvent such as acetonitrile, ethylene glycol or a mixture of these solvents and at a temperature between the ambient temperature and the reflux temperature of the solvent.

A compound of formula (I) in which $R_3$ represents a group —$CH_2NR_8CONR_{14}R_{15}$ in which $R_8$=$R_{14}$=$R_{15}$ =H may also be prepared by reacting a compound of formula (I) in which $R_3$=—$CH_2NH_2$ with trimethylsilyl isocyanate in a solvent such as dichloromethane at a temperature between the ambient temperature and the reflux temperature of the solvent, followed by hydrolysis in an acidic medium.

A compound of formula (I) in which $R_3$ represents a group —$CONR_{16}R_{17}$ may also be prepared by reacting a corresponding intermediate in which $R_3$ represents a carboxyl with a compound of formula $HNR_{16}R_{17}$ by conventional methods of peptide coupling; the corresponding intermediate is prepared by conventional methods by acid or base treatment of a compound of formula (I) in which $R_3$ represents a ($C_1$-$C_4$)alkoxycarbonyl or by reacting a compound of formula (Ia) with a strong base such as an alkali metal hydroxide such as potassium hydroxide in a solvent such as toluene or ethylene glycol at a temperature between the ambient temperature and the reflux temperature of the solvent.

A compound of formula (I) in which $R_3$ represents a group —$NR_8COR_9$ in which $R_9$=—$(CH_2)_m$—$NR_6R_7$ may also be prepared by reacting a corresponding intermediate in which $R_3$ represents a group —$NR_8CO(CH_2)_m$-Hal and Hal represents a halogen atom, preferably chlorine, with an excess of a compound of formula $HNR_6R_7$ in a solvent such as dichloromethane or ethanol at a temperature between the ambient temperature and the reflux temperature of the solvent; the corresponding intermediate is prepared, by reacting a compound of formula (I) in which $R_3$=—$NHR_8$ with a compound of formula Hal-CO—$(CH_2)_m$-Hal in which Hal represents a halogen atom, preferably chlorine or bromine, in the presence of a base such as triethylamine or N,N- diisopropylethylamine in a solvent such as dichloromethane and at a temperature between 0° C. and the ambient temperature.

A compound of formula (I) in which $R_3$ represents a group —$CH_2OR_5$ in which $R_5$ represents a hydrogen atom may also be prepared by acid or base treatment of a compound of formula (I) in which $R_3$ represents a group —$CH_2OR_5$ in which $R_5$ represents a ($C_1$-$C_4$) alkylcarbonyl.

The compounds of formula (I) thus obtained may be subsequently separated from the reaction medium and purified by conventional methods, for example by crystallization or chromatography.

The compounds of formula (I) thus obtained are isolated in the form of the free base or a salt, by conventional techniques.

The compounds of formula (IIa) are prepared by reacting a piperidine derivative of formula

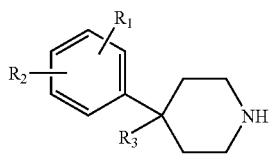

(IV)

in which $R_1$, $R_2$ and $R_3$ are as defined for a compound of formula (I) with a compound of formula

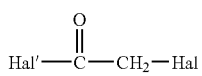

(V)

in which Hal and Hal' represent each independently a halogen atom, preferably chlorine or bromine. The reaction is carried out in the presence of a base such as triethylamine, N,N-diisopropylethylamine or N-methylmorpholine in a solvent such as dichloromethane, chloroform, tetrahydrofuran, dioxane or a mixture of these solvents and at a temperature between 0° C. and the ambient temperature.

The compounds of formula (IIb) are prepared by reacting the compound of formula (IV) with a compound of formula

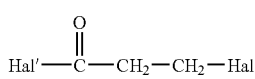

(VI)

in which Hal and Hal' are as defined above under the operating conditions mentioned above.

Similarly the compounds of formula (IIc) or (IId) respectively are prepared by reacting a compound of formula

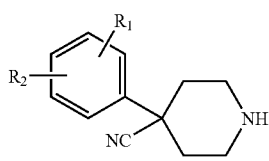

(IVa)

in which $R_1$ and $R_2$ are as defined for a compound of formula (I) with a compound of formula (V) or (VI) respectively in accordance with the same operating conditions as above.

The compounds of formula (V) or (VI) are available commercially, are known or are prepared by known methods.

The compound of formula (III) is prepared by known methods such as those described in J. Org. Chem., 1953, 18, 1484-1488, J. Med. Chem., 1978, 21 (6), 536-542, Chem. Pharm. Bull., 1991, 39 (9), 2288-2300, Tetrahedron Letters, 1998, 39, 617-620 or in WO 97/28129.

For example, a compound of formula (III) is prepared by reacting a compound of formula

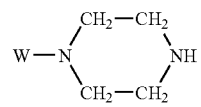

(VII)

in which W represents hydrogen or an N-protective group with a compound of formula Hal-$R_4$     (VIII)

in which $R_4$ is as defined for a compound of formula (I) and Hal represents a halogen atom, preferably chlorine, bromine or iodine.

The reaction is carried out in the presence or absence of a base, in an inert solvent such as ethanol, propan-2-ol, n-butanol, acetonitrile or toluene at a temperature between 0° C. and the reflux temperature of the solvent. When a base is used it is selected from organic bases such as diisopropylethylamine or from alkali metal carbonates such as sodium or potassium carbonate. In the absence of a base the reaction is carried out using an excess of the compound of formula (VII). The reaction may also be carried out without solvent, by heating the mixture of compounds (VII) and (VIII) at temperatures of the order of from 140° C. to 180° C.

Where appropriate, when W represents an N-protective group, it is eliminated by conventional methods to give the expected compounds of formula (III).

The compounds of formula (VII) or of formula (VIII) are known or are prepared by known methods. The compounds of formula (IV) are available commercially, are known or are prepared by known methods such as those described in EP-0 474 561, EP-0 673 928 or WO 96/23787.

The compounds of formula (IV) are generally prepared in a form in which they are protected on the nitrogen atom of the piperidine; after a step of deprotection the compounds of formula (IV) themselves are obtained.

In particular a compound of formula (IV) in which $R_3$ represents a group —$OR_5$ in which $R_5$=H is prepared by reacting an organomagnesium derivative of formula

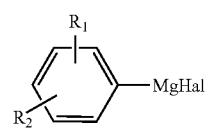

(IX)

in which $R_1$ and $R_2$ are as defined for a compound of formula (I) and Hal represents a halogen atom, preferably bromine, with 1-benzyl-4-piperidinone in a solvent such as diethyl ether or tetrahydrofuran at a temperature between the ambient temperature and reflux temperature of the solvent.

The organomagnesium derivatives of formula (IX) are prepared by conventional methods well known to the person skilled in the art from the corresponding halogenated derivatives.

From compounds of formula (IV) in which $R_3$=—OH the compounds of formula (IV) in which $R_3$=—$OR_5$ in which $R_5$ represents a ($C_1$-$C_4$)alkyl or a ($C_1$-$C_4$)alkylcarbonyl, respectively, are prepared by an alkylation or acylation reaction, respectively, by methods which are known to the person skilled in the art.

The compounds of formula (IV) in which $R_3$=—OH and which carry a protective group on the nitrogen atom of the piperidine may undergo a Ritter reaction by the action of acetonitrile in an acidic medium in order to prepare the compounds of formula (IV) in which $R_3$=—$NHCOCH_3$ by the method described in EP-0 474 561. Hydrolysis in a strong acidic medium is then used to prepare the compounds of formula (IV) in which $R_3$=—$NR_6R_7$ in which $R_6$=$R_7$=H. The methods described in EP-0 673 928 or WO 96/23787 are used to prepare the compounds of formula (IV) in which $R_3$=—$NR_6R_7$ in which $R_6$ and/or $R_7$ represents a ($C_1$-$C_4$) alkyl.

The compounds of formula (IV) in which $R_3$=—$NR_8COR_9$ in which $R_9$ is a ($C_1$-$C_4$)alkyl, or else $R_3$=—$NR_8CONR_{10}R_{11}$, or else $R_3$=—$CH_2NR_{12}R_{13}$ in which $R_{12}$ and $R_{13}$ represent each independently a hydrogen or a ($C_1$-$C_4$)alkyl, or else $R_3$=—$CH_2NR_8CONR_{14}R_{15}$, or else $R_3$=($C_1$-$C_4$)alkoxycarbonyl, or else $R_3$=—$CONR_{16}R_{17}$ are prepared by the methods described in WO 96/23787.

A compound of formula (IV) in which $R_3$=—$CH_2NR_{12}R_{13}$ in which $R_{12}$=$R_{13}$=H is prepared from the compound of formula (IVa) by the method described above for a compound of formula (I).

A compound of formula (IV) in which $R_3$=—$NR_8COR_9$ in which $R_9$=—$(CH_2)_mNR_6R_7$ is prepared by the method described above for a compound of formula (I).

A compound of formula (IV) in which $R_3$=—$CH_2NR_{12}R_{13}$ in which $R_{12}$=H or ($C_1$-$C_5$) alkyl and $R_{13}$=($C_1$-$C_5$)alkyl, a group —$(CH_2)_q$—OH or a group —$(CH_2)_q$—S—$CH_3$ is prepared by the method described above for a compound of formula (I).

A compound of formula (IV) in which $R_3$=—$CH_2NR_{12}R_{13}$ in which $R_{12}$=H and $R_{13}$=—$CH_3$ may also be prepared by reducing a corresponding intermediate in which $R_3$=—$CH_2NHCHO$ using a reducing agent such as lithium aluminium hydride in a solvent such as ether or tetrahydrofuran at a temperature between the ambient temperature and the reflux temperature of the solvent. The corresponding intermediate is prepared by reacting a compound of formula (IV) in which $R_3$=—$CH_2NH_2$ with ethyl formate at a temperature between the ambient temperature and 60° C.

A compound of formula (IV) in which $R_3$=—$CH_2NR_{12}R_{13}$ in which $R_{12}$ and $R_{13}$, together with the nitrogen atom to which they are attached, constitute aziridine, azetidine, pyrrolidine, piperidine or morpholine is prepared by the methods described above for a compound of formula (I).

A compound of formula (IV) in which $R_3$=—$CONR_{16}R_{17}$ in which $R_{16}$=$R_{17}$=H may also be prepared by reacting a compound of formula (IVa), protected on the nitrogen atom of the piperidine, with hydrogen peroxide in the presence of a strong base such as an alkali metal hydroxide such as sodium hydroxide and a phase transfer catalyst such as a substituted quaternary ammonium salt, triethylammonium chloride for example, in a solvent such as toluene in a mixture with water, at a temperature between the ambient temperature and the reflux temperature of the solvent.

The compounds of formula (IVa) are prepared by known methods such as those described in Bioorg. Med. Chem. Lett., 1999, 9, 3273-3276 and in J. Med. Chem., 1999, 42 (23), 4778-4793.

From compounds of formula (IV) in which $R_3$=—$CH_2OH$ the compounds of formula (IV) in which $R_3$=—$CH_2OR_5$ in which $R_5$ represents a ($C_1$-$C_4$)alkyl or a ($C_1$-$C_4$)alkylcarbonyl, respectively, are prepared by an alkylation or acylation reaction, respectively, by the methods known to the person skilled in the art.

The compounds of formula (IV) in which $R_3$=—$CH_2OR_5$ in which $R_5$ represents a hydrogen atom are prepared by reducing a compound of formula (IV) in which $R_3$ represents a methoxycarbonyl by methods known to the person skilled in the art.

The compounds of formula (IV) in which $R_3$ represents a ($C_1$-$C_4$)alkoxycarbonyl are prepared by esterification reaction of a corresponding intermediate in which $R_3$ represents a carboxyl by methods known to the person skilled in the art; the corresponding intermediate is prepared by reacting a compound of formula (VIa) with a strong base such as an alkali metal hydroxide such as potassium hydroxide, in a solvent such as toluene or ethylene glycol at a temperature between the ambient temperature and the reflux temperature of the solvent.

During any of the steps of preparing the compounds of formula (I), or of the intermediates of formula (Ia), (IIa), (IIb), (IIc), (IId), (III) or (IV), it may be necessary and/or desirable to protect the sensitive or reactive functional groups, such as the amine, hydroxyl or carboxyl groups, which are present on any of the molecules concerned. This protection may be carried out using the conventional protective groups, such as those described in Protective Groups in Organic Chemistry, J. F. W. McOmie, Ed., Plenum Press, 1973, in Protective Groups in Organic Synthesis, T. W. Greene and P. G. M. Wutts, Ed., John Wiley & Sons, 1991 or in Protecting Groups, Kocienski P. J., 1994, Georg Thieme Verlag. The protective groups can be eliminated in an appropriate subsequent step, using the methods which are known to the person skilled in the art and which are not to the detriment of the rest of the molecule in question.

The N-protective groups used where appropriate are conventional N-protective groups which are well known to the person skilled in the art, such as, for example, the tert-butoxycarbonyl, fluorenylmethoxycarbonyl, benzyl, benzhydrylidene or benzyloxycarbonyl group.

The invention, in another of its aspects, further provides the compounds of formula (Ia). These compounds are useful as synthesis intermediates for the compounds of formula (I).

Accordingly, in another of its aspects, the invention provides compounds of formula

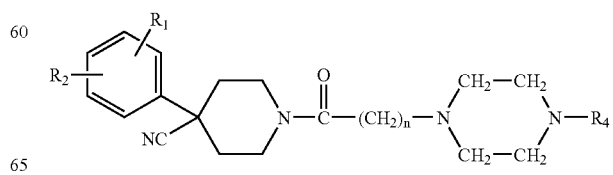

(Ia)

in which n is 1 or 2;

R$_1$ represents a halogen atom; a trifluoromethyl radical; a (C$_1$-C$_4$)alkyl; a (C$_1$-C$_4$)alkoxy; a trifluoromethoxy radical;

R$_2$ represents a hydrogen atom or a halogen atom;

R$_4$ represents the aromatic group 1,3-thiazol-2-yl of formula:

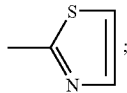

in the form of a base or an addition salt with an acid, and also in the form of a hydrate or solvate.

The following examples describe the preparation of certain compounds in accordance with the invention. These examples are not limitative and merely illustrate the present invention. The numbers of the compounds exemplified refer to those given in Table I below, which illustrates the chemical structures and the physical properties of some compounds according to the invention.

In the preparations and in the examples the following abbreviations are used:

ether: diethyl ether
iso ether: diisopropyl ether
DMSO: dimethyl sulphoxide
DMF: N,N-dimethylformamide
THF: tetrahydrofuran
DCM: dichloromethane
AcOEt: ethyl acetate
DIPEA: diisopropylethylamine
TFA: trifluoroacetic acid
BOP: benzotriazol-1-yloxytris(dimethylamino)-phosphonium hexafluorophosphate
PyBOP: benzotriazol-1-yloxytripyrrolidino-phosphonium hexafluorophosphate
2N hydrochloric ether: 2N solution of hydrochloric acid in diethyl ether
m.p.: melting point
AT: ambient temperature
b.p.: boiling temperature
HPLC: high performance liquid chromatography
Silica H: Silica gel 60 H sold by Merck (Darmstadt)
Buffer solution pH=2: solution of 16.66 g of KHSO$_4$ and 32.32 g of K$_2$SO$_4$ in one litre of water.

The proton magnetic resonance ($^1$H NMR) spectra are recorded at 200 MHz in DMSO-d$_6$, using the DMSO-d$_6$ peak as reference. The chemical shifts δ are expressed in parts per million (ppm). The signals observed are expressed as follows: s: singlet; bs: broad singlet; d: doublet; sd: split doublet; t: triplet; st: split triplet; q: quadruplet; unres. comp.: unresolved complex; mt: multiplet.

The NMR spectra confirm the structures of the compounds.

The compounds according to the invention are analysed by LC/UV/MS (liquid chromatography/UV detection/mass spectrometry) coupling.

For the compounds a check is made that their mass spectra as obtained in the positive electrospray mode (ESI+) are compatible with the calculated molar mass.

The mass spectra of the compounds according to the invention generally have as their base peak the molecular ion MH$^+$.

PREPARATIONS

1. Preparations of Compounds of Formulae (IV) and (IVa)

Preparation 1.1

4-[3-(Trifluoromethyl)phenyl]-4-piperidinol hydrochloride (IV), HCl: R$_1$=3-CF$_3$; R$_2$=H; R$_3$=—OH.

A) 1-Benzyl-4-[3-(trifluoromethyl)phenyl]-4-piperidinol hydrochloride

A mixture of 180 g of magnesium in 2670 ml of THF is heated to 30° C. and admixed with 33 ml of a solution of 1670 g of 1-bromo-3-(trifluoromethyl)benzene in 1330 ml of THF and then, slowly, with the remainder of the solution so as to bring about and subsequently maintain reflux of the THF, and is left at reflux with stirring for 2 hours. Subsequently a solution of 1000 g of 1-benzyl-4-piperidinone in 3200 ml of THF is added slowly and the mixture is heated at reflux for 2 hours. After cooling to AT, the reaction mixture is introduced over 30 minutes into a solution of 1870 g of ammonium chloride in 6700 ml of water and the mixture is left with stirring at 20-25° C. for 2 hours. After decanting, the organic phase is washed with 5330 ml of water and the solvent is evaporated under vacuum. The residue is taken up in 5330 ml of ether, a solution of 210 g of HCl gas in 800 ml of propan-2-ol is added slowly, the temperature being kept below 25° C., the mixture is left with stirring for 40 minutes and the crystals formed are isolated with suction. The crystals are taken up in 2000 ml of ether and again isolated with suction. 1080 g of the expected product are obtained following recrystallization from a propan-2-ol/EtOH (70/30; v/v) mixture.

B) 4-[3-(Trifluoromethyl)phenyl]-4-piperidinol hydrochloride.

A mixture of 1000 g of the compound obtained in the preceding step and 83 g of 10% palladium on carbon (50% moisture content) in 2910 ml of EtOH and 2910 ml of MeOH is hydrogenated at 50° C. under a pressure of 2 bars. The catalyst is filtered off and washed twice with 660 ml of MeOH and the filtrate and washings are concentrated under vacuum. The residue is taken up in 3320 ml of ether and is left with stirring at AT for 1 hour 30 minutes. The precipitate formed is isolated with suction, washed with 280 ml of ether and dried under vacuum at 40° C. This gives 726 g of the expected product.

Preparation 1.2

4-Methoxy-4-[3-(trifluoromethyl)phenyl]-piperidine (IV): R$_1$=3-CF$_3$; R$_2$=H; R$_3$=—OCH$_3$.

A) tert-Butyl 4-hydroxy-4-[3-(trifluoromethyl)phenyl]-1-piperidinecarboxylate.

20 g of the compound obtained in Preparation 1.1 in 80 ml of DCM is admixed at AT with 17.92 g of triethylamine and then, dropwise, with a solution of 16.3 g of di-tert-butyl dicarbonate in 20 ml of DCM and the mixture is left with stirring at AT for 18 hours. Water is added to the reaction mixture, which is then extracted with DCM, the organic phase is washed with water and a 5% KHSO$_4$ solution and dried over Na$_2$SO$_4$ and the solvent is evaporated under vacuum. This gives 13 g of the expected product following recrystallization from an iso ether/hexane mixture.

B) tert-Butyl 4-methoxy-4-[3-(trifluoromethyl)phenyl]-1-piperidinecarboxylate.

A solution of 2 g of the compound obtained in the preceding step in 15 ml of DMF and 20 ml of THF is admixed, in portions and at AT, with 0.277 g of sodium hydride at a concentration of 60% in oil and the mixture is left with stirring for 40 minutes. Subsequently 1.3 g of methyl iodide are added and the mixture is left with stirring for 2 hours. The reaction mixture is concentrated under vacuum, the residue is taken up with water and extracted with AcOEt, the organic phase is washed with water and dried over $Na_2SO_4$ and the solvent is evaporated under vacuum. This gives 2 g of the expected product in the form of a yellow oil.

C) 4-Methoxy-4-[3-(trifluoromethyl)phenyl]piperidine.

A mixture of 2 g of the compound obtained in the preceding step and 5 ml of TFA in 15 ml of DCM is left with stirring at AT for 1 hour. The reaction mixture is concentrated under vacuum, the residue is extracted with DCM, the organic phase is washed with a 5% $Na_2CO_3$ solution and dried over $Na_2SO_4$ and the solvent is evaporated under vacuum. This gives 1.7 g of the expected product in the form of an orange-coloured oil.

Preparation 1.3

N,N-Dimethyl-4-[3-(trifluoromethyl)phenyl]-4-piperidineamine.

(IV): $R_1$=3-$CF_3$; $R_2$=H; $R_3$=—N($CH_3$)$_2$.

A) 1-Benzyl-4-[3-(trifluoromethyl)phenyl]-4-piperidinol.

An icebath is used to cool a solution of 20 g of the compound obtained in Preparation 1.1 (free base) and 11.3 ml of triethylamine in 200 ml of DCM, 11 ml of benzyl bromide are added dropwise and the mixture is left with stirring at AT overnight. It is concentrated under vacuum, the residue is taken up in saturated $K_2CO_3$ solution and extracted with AcOEt, the organic phase is washed with saturated $K_2CO_3$ solution and with saturated NaCl solution and dried over $Na_2SO_4$ and the solvent is evaporated under vacuum. The oily residue is taken up in pentane and the precipitate formed is isolated with suction. This gives 17 g of the expected product.

B) N-[1-Benzyl-4-[3-(trifluoromethyl)phenyl]-4-piperidyl]acetamide.

An icebath is used to cool 60 ml of concentrated $H_2SO_4$, a solution of 16 g of the compound obtained in the preceding step in 120 ml of acetonitrile is added dropwise, during which the temperature of the reaction medium is kept below 30° C. and the mixture is left with stirring overnight, during which the temperature is allowed to return to AT. The reaction mixture is poured onto ice and rendered alkaline by addition of concentrated NaOH solution and the precipitate formed is isolated with suction. The precipitate is dissolved in DCM, the organic phase is washed with water and dried over $Na_2SO_4$ and the solvent is evaporated under vacuum. This gives 9.7 g of the expected product following recrystallization from acetonitrile.

C) 1-Benzyl-4-[3-(trifluoromethyl)phenyl]-4-piperidineamine.

A mixture of 9.6 g of the compound obtained in the preceding step, 250 ml of concentrated HCl solution and 250 ml of water is heated at 150° C. overnight. Half of the reaction mixture is concentrated under vacuum, the resulting acidic aqueous phase is rendered alkaline by addition of concentrated NaOH solution and extracted with DCM, the organic phase is dried over $Na_2SO_4$ and the solvent is evaporated under vacuum. This gives 8.1 g of the expected product, which is used as it is.

D) 1-Benzyl-N,N-dimethyl-4-[3-(trifluoromethyl)phenyl]-4-piperidineamine.

A mixture of 8.1 g of the compound obtained in the preceding step, 3.5 ml of a 37% solution of formaldehyde in water and 10 ml of acetic acid in 250 ml of THF is admixed in portions and at AT with 50 g of sodium triacetoxyborohydride and the mixture is left with stirring at AT overnight. 200 ml of MeOH are added and the reaction mixture is heated at 70° C. for 1 hour and concentrated under vacuum. The residue is taken up with 1N NaOH solution and extracted with DCM, the organic phase is washed with water and dried over $Na_2SO_4$ and the solvent is evaporated under vacuum. This gives 8.7 g of the expected product in the form of an oil which solidifies.

E) N,N-Dimethyl-4-[3-(trifluoromethyl)phenyl]-4-piperidineamine.

A mixture of 8.2 g of the compound obtained in the preceding step, 5 g of ammonium formate and 2 g of 10% palladium on carbon in 100 ml of MeOH is left with stirring at AT for 1 hour. The catalyst is filtered off and the filtrate is concentrated under vacuum. The residue is taken up with saturated $K_2CO_3$ solution and extracted with AcOEt, the organic phase is dried over $Na_2SO_4$ and the solvent is evaporated under vacuum. This gives 4.8 g of the expected product.

Preparation 1.4

4-[3-(Trifluoromethyl)phenyl]-4-piperidine-carbonitrile hydrochloride.

(IVa), HCl: $R_1$=3-$CF_3$; $R_2$=H.

A) 2-(2,2-Diethoxyethyl)-4,4-diethoxy-2-[3-(trifluoromethyl)phenyl]butanenitrile.

A mixture of 30 g of 3-trifluoromethyl)-phenylacetonitrile and 14.4 g of sodium amide in 400 ml of toluene is left with stirring at AT for 5 minutes, 66 ml of bromoacetaldehyde diethyl acetal are added and the mixture is then heated at 60° C. for 3 hours. It is concentrated under vacuum, the residue is taken up in water and extracted with ether, the organic phase is dried over $Na_2SO_4$ and the solvent is evaporated under vacuum. The residue is chromatographed on silica gel H, eluting with a DCM/AcOEt (100/5; v/v) mixture. This gives 26 g of the expected product.

B) 4-Oxo-2-(2-oxoethyl)-2-[3-(trifluoromethyl)-phenyl]butanenitrile.

A mixture of 23.9 g of the compound obtained in the preceding step in 90 ml of formic acid is left with stirring at 50° C. for 1 hour. Water is added to the reaction mixture, which is then extracted with AcOEt, the organic phase is washed with water and with 10% $NaHCO_3$ solution and dried over $Na_2SO_4$ and the solvent is evaporated under vacuum. This gives 16 g of the expected product, which is used immediately in the following step.

C) 1-Benzyl-4-[3-(trifluoromethyl)phenyl]-4-piperidinecarbonitrile hydrochloride.

A mixture of 16 g of the compound obtained in the preceding step, 6.25 ml of benzylamine, 48.6 g of sodium triacetoxyborohydride and 5 drops of acetic acid in 150 ml of DCM is left with stirring at AT overnight. Subsequently 40 ml of MeOH are added dropwise and the mixture is then heated at 60° C. for 1 hour. The reaction mixture is concentrated under vacuum, the residue is extracted with AcOEt, the organic phase is washed with 10% NaHCO₃ solution and with water and dried over Na₂SO₄ and the solvent is evaporated under vacuum. The residue is taken up in a saturated solution of HCl gas in ether and the precipitate formed is isolated with suction. This gives 18 g of the expected product.

D) 4-[3-(Trifluoromethyl)phenyl]-4-piperidine-carbonitrile hydrochloride.

A mixture of 2 g of the compound obtained in the preceding step and 0.2 g of 10% palladium on carbon in 30 ml of MeOH is hydrogenated at AT at atmospheric pressure for 3 hours. The catalyst is filtered off on Celite® and the filtrate is concentrated under vacuum. This gives 1.5 g of the expected product.

This compound can also be prepared by following the three steps below:

A') tert-Butyl bis(2-chloroethyl)carbamate.

A mixture of 106 g of N,N-bis(2-chloroethyl)amine hydrochloride and 130 g of di-tert-butyl dicarbonate in 1 500 ml of DCM is admixed dropwise over 1 hour 30 minutes at AT with 83 ml of triethylamine, then left with stirring at AT overnight. The reaction mixture is washed with water and the organic phase is dried over Na₂SO₄ and evaporated under vacuum. This gives 150 g of the expected product, which is used as it is.

B') tert-Butyl 4-cyano-4-[3-(trifluoromethyl)phenyl]-1-piperidine carboxylate.

A suspension of 56 g of sodium hydride at a concentration of 60% in oil in 750 ml of DMSO in 250 ml of THF is admixed dropwise under an inert atmosphere and at AT with a solution of 120 g of 3-(trifluoromethyl)phenylacetonitrile in 250 ml of DMSO and then, slowly with a solution of 150 g of the compound obtained in the preceding step in 250 ml of DMSO and heated at 60° C. overnight. The reaction mixture is poured into an ice/H₂O mixture and extracted with ether, the organic phase is washed with water and with saturated NaCl solution and dried over Na₂SO₄ and the solvent is evaporated under vacuum. The residue is chromatographed on silica gel, eluting with DCM and then with a DCM/AcOEt (80/20; v/v) mixture. This gives 191 g of the expected product, which crystallizes; m.p.=72-73° C.

C') 4-[3-(Trifluoromethyl)phenyl]-4-piperidine-carbonitrile hydrochloride.

A mixture of 115 g of the compound obtained in the preceding step, 500 ml of a 2N solution of HCl in ether and 150 ml of MeOH is left with stirring at AT for 4 hours. The crystalline product formed is isolated with suction and dried. This gives 75 g of the expected product, m.p.=259° C.

Preparation 1.5 tert-Butyl [4-[3-(trifluoromethyl)phenyl]-4-piperidyl]methylcarbamate.

(IV): $R_1$=3-$CF_3$; $R_2$=H; $R_3$=—$CH_2NH$—COOC($CH_3$)$_3$.

A) [1-Benzyl-4-[3-(trifluoromethyl)phenyl]-4-piperidyl]methylamine.

A mixture of 1.5 g of the compound obtained in step C of preparation 1.4, 0.15 g of Raney® nickel and 5 ml of aqueous ammonia in 20 ml of MeOH is hydrogenated at AT under atmospheric pressure overnight. The catalyst is filtered off and the filtrate is concentrated under vacuum. This gives 1.45 g of the expected product.

B) tert-Butyl [1-benzyl-4-[3-(trifluoromethyl)-phenyl]-4-piperidyl]methylcarbamate.

A mixture of 1.45 g of the compound obtained in the preceding step and 20 ml of AcOEt is heated to 40° C., 0.9 g of di-tert-butyl dicarbonate is added and the mixture is then heated at reflux for 30 minutes. After cooling to AT it is admixed with water and extracted with AcOEt, the organic phase is dried over Na₂SO₄ and the solvent is evaporated under vacuum. This gives 1.86 g of the expected product.

C) tert-Butyl [4-[3-(trifluoromethyl)phenyl]-4-piperidyl]methylcarbamate.

A mixture of 1.8 g of the compound obtained in the preceding step and 0.18 g of 10% palladium on carbon in 20 ml of MeOH is hydrogenated at AT at atmospheric pressure overnight. The catalyst is filtered off and the filtrate is concentrated under vacuum. This gives 1.3 g of the expected product in the form of an oil.

Preparation 1.6

4-[3-(Trifluoromethyl)phenyl]-4-piperidinecarboxamide.

(IV): $R_1$=3-$CF_3$; $R_2$=H; $R_3$=—$CONH_2$.

A) 1-Benzyl-4-[3-(trifluoromethyl)phenyl]-4-piperidinecarboxamide.

A mixture of 5 g of the compound obtained in step C of preparation 1.4, 30 ml of toluene, 30 ml of 30% $H_2O_2$ solution, 30 ml of 30% NaOH solution and 0.5 g of aliquot 336 (trioctylmethylammonium chloride) is heated at 100° C. for 48 hours. It is concentrated under vacuum, the residue is taken up in water and extracted with DCM, the organic phase is dried over Na₂SO₄ and the solvent is evaporated under vacuum. The residue is chromatographed on silica gel H, eluting with a DCM/MeOH (100/3; v/v) mixture. This gives 2.5 g of the expected product.

B) 4-[3-(Trifluoromethyl)phenyl]-4-piperidine-carboxamide.

A mixture of 2.5 g of the compound obtained in the preceding step and 0.25 g of 10% palladium on carbon in 30 ml of MeOH is hydrogenated at AT under atmospheric pressure for 48 hours. The catalyst is filtered off and the filtrate is concentrated under vacuum. This gives 1.7 g of the expected product.

Preparation 1.7

4-[2-(Trifluoromethyl)phenyl]-4-piperidinol (IV): $R_1$=2-$CF_3$; $R_2$=H; $R_3$=—OH.

A) 1-Benzyl-4-[2-(trifluoromethyl)phenyl]-4-piperidinol.

A mixture of 1.52 g of magnesium in 25 ml of THF is admixed dropwise over 20 minutes with a solution of 14.25 g of 1-bromo-2-(trifluoromethyl)benzene in 15 ml of THF and the mixture is heated at reflux for 30 minutes. After it has cooled on an ice bath, it is admixed slowly with a solution of 10 g of 1-benzyl-4-piperidinone in 30 ml of THF and left with stirring at AT for 3 hours. The reaction mixture is poured into saturated aqueous ammonium chloride solution and extracted with AcOEt, the combined organic phases are washed with water and dried over Na₂SO₄ and the solvents are evaporated under vacuum. The residue is chromatographed on silica gel, eluting with a DCM/AcOEt (70/30; v/v) mixture. This gives 4.5 g of the expected product.

B) 4-[2-(Trifluoromethyl)phenyl]-4-piperidinol.

A mixture of 4.5 g of the compound obtained in the preceding step and 0.5 g of 10% palladium on carbon in 100 ml of MeOH is hydrogenated at 35° C. under atmospheric pressure overnight. The catalyst is filtered off and the filtrate is concentrated under vacuum. This gives 2.7 g of the expected product following recrystallization from iso ether.

Preparation 1.8

4-[2-(trifluoromethyl)phenyl]-4-piperidinecarbonitrile hydrochloride (IVa), HCl: $R_1$=2-$CF_3$; $R_2$=H.

A) tert-Butyl 4-cyano-4-[2-(trifluoromethyl)phenyl]-1-piperidinecarboxylate.

A suspension of 9 g of sodium hydride at a concentration of 60% in oil in 125 ml of DMSO and 125 ml of THF is admixed dropwise and at AT with a solution of 20 g of 2-(trifluoromethyl)phenyl-acetonitrile in 50 ml of DMSO and then, slowly, with a solution of 25 g of the compound obtained in step A' of preparation 1.4 in 70 ml of DMSO and the mixture is heated at 60° C. for 24 hours. The reaction mixture is poured into 2 litres of water and extracted with ether, the organic phase is washed with water and dried over $Na_2SO_4$ and the solvent is evaporated under vacuum. The residue is chromatographed on silica gel, eluting with DCM and then with a DCM/AcOEt (70/30; v/v) mixture. This gives 16 g of the expected product.

B) 4-[2-(Trifluoromethyl)phenyl]-4-piperidine-carbonitrile hydrochloride.

A mixture of 6 g of the compound obtained in the preceding step, 150 ml of 2N hydrochloric ether and 20 ml of MeOH is left with stirring at AT for 2 hours. It is concentrated under vacuum, the residue is taken up in ether and the precipitate formed is isolated with suction. This gives 2.3 g of the expected product.

Preparation 1.9

Methyl 4-[3-(trifluoromethyl)phenyl]-4-piperidinecarboxylate hydrochloride (IV), HCl: $R_1$=3-$CF_3$; $R_2$=H; $R_3$=—$COOCH_3$.

A) 1-Benzyl-4-[3-(trifluoromethyl)phenyl]-4-piperidinecarboxylic acid.

A mixture of 5 g of the compound obtained in step C of preparation 1.4 and 4.25 g of KOH pellets in 80 ml of ethylene glycol is heated at reflux for 3 hours. It is cooled to AT and admixed with 100 ml of water, acidified to pH=6.5 by addition of 10% HCl solution, and the precipitate formed is isolated with suction and dried under vacuum. This gives 3.9 g of the expected product, m.p.=243° C.

B) Methyl 1-benzyl-4-[3-(trifluoromethyl)phenyl]-4-piperidinecarboxylate hydrochloride.

A mixture of 3 g of the compound obtained in the preceding step and 50 ml of thionyl chloride in 100 ml of DCM is heated at 60° C. for 3 hours. It is concentrated under vacuum and the residue is taken up in 100 ml of MeOH and heated at 60° C. overnight. Concentration under vacuum gives 4 g of the expected product, m.p.=230° C.

C) Methyl 4-[3-(trifluoromethyl)phenyl]-4-piperidinecarboxylate hydrochloride.

A mixture of 4 g of the compound obtained in the preceding step and 0.4 g of 10% palladium on carbon in 200 ml of MeOH is hydrogenated at AT under atmospheric pressure overnight. The catalyst is filtered off and the filtrate is concentrated under vacuum. This gives 2.5 g of the expected product.

Preparation 1.10

[4-[3-(Trifluoromethyl)phenyl]-4-piperidyl]methyl acetate.

(IV): $R_1$=3-$CF_3$; $R_2$=H; $R_3$=—$CH_2$—O—CO—$CH_3$.

A) 1-(tert-Butyl)-4-methyl 4-[3-(trifluoromethyl)-phenyl]-1,4-piperidinedicarboxylate.

A mixture of 7 g of the compound obtained in preparation 1.9, 5.33 g of di-tert-butyldicarbonate and 3.5 ml of triethylamine in 100 ml of DCM is left with stirring at AT for 2 hours. It is concentrated under vacuum, the residue is taken up in water and extracted with ether, the organic phase is washed with water and dried over $Na_2SO_4$ and the solvent is evaporated under vacuum. This gives 9.3 g of the expected product.

B) tert-Butyl 4-(hydroxymethyl)-4-[3-(trifluoromethyl)phenyl]-1-piperidinecarboxylate.

A mixture of 9.27 g of the compound obtained in the preceding step in 150 ml of ether is cooled to 0° C., 1 g of lithium aluminium hydride is added and the mixture is left with stirring at 0° C. for 4 hours. The reaction mixture is admixed with saturated $NH_4Cl$ solution, the mineral salts are filtered off, the filtrate is extracted with AcOEt, the organic phase is dried over $Na_2SO_4$ and the solvent is evaporated under vacuum. This gives 5.5 g of the expected product following recrystallization from ether.

C) tert-Butyl 4-[(acetyloxy)methyl]-4-[3-(trifluoromethyl)phenyl]-1-piperidinecarboxylate.

A mixture of 5.5 g of the compound obtained in the preceding step and 2 ml of triethylamine in 50 ml of DCM is cooled to −70° C., 1.1 ml of acetyl chloride are added and the mixture is left with stirring overnight, during which the temperature is allowed to return to AT. Ice is added to the reaction mixture, which is then extracted with DCM, the organic phase is dried over $Na_2SO_4$ and the solvent is evaporated under vacuum. This gives 6 g of the expected product.

D) [4-[3-(Trifluoromethyl)phenyl]-4-piperidyl]methyl acetate.

A mixture of 6 g of the compound obtained in the preceding step and 30 ml of TFA in 50 ml of DCM is left with stirring at AT for 1 hour. It is concentrated under vacuum, the residue is taken up with ice and then with 10% $NaHCO_3$ solution and extracted with DCM, the organic phase is dried over $Na_2SO_4$ and the solvent is evaporated under vacuum. This gives 4.5 g of the expected product.

Preparation 1.11

4-[4-(Trifluoromethyl)phenyl]-4-piperidinol (IV): $R_1$=4-$CF_3$; $R_2$=H; $R_3$=—OH.

A) 1-Benzyl-4-[4-(trifluoromethyl)phenyl]-4-piperidinol.

This compound is prepared by the procedure described in step A of preparation 1.7, from 1.55 g of magnesium in 25 ml of THF, a solution of 14.25 g of 1-bromo-4-(trifluoromethyl)benzene in 15 ml of THF and a solution of 10 g of 1-benzyl-4-piperidinone in 30 ml of THF. This gives 7.3 g of the expected product.

B) 4-[4-(Trifluoromethyl)phenyl]-4-piperidinol.

A mixture of 4.8 g of the compound obtained in the preceding step and 2 g of 10% palladium on carbon in 50 ml of MeOH is hydrogenated at 30° C. under atmospheric pressure for 2 hours. The catalyst is filtered off and the filtrate is concentrated under vacuum. This gives 2.4 g of the expected product following recrystallization from iso ether.

Preparation 1.12

4-(4-Chlorophenyl)-4-piperidinecarbonitrile hydrochloride (IVa), HCl: $R_1$=4-Cl; $R_2$=H.

A) tert-Butyl 4-(4-chlorophenyl)-4-cyano-1-piperidinecarboxylate.

A suspension of 4.4 g of sodium hydride at a concentration of 60% in oil in 300 ml of THF is admixed rapidly at AT with 7.51 g of 4-chlorophenylacetonitrile and then with 12 g of tert-butyl bis(2-chloroethyl)-carbamate, heated at 40° C. for 28 hours and then left with stirring at AT overnight. Saturated ammonium chloride solution is added to the reaction mixture, which is then concentrated under vacuum to remove the THF, after which the aqueous phase which remains is extracted with ether, the organic phase is washed with a buffer solution pH=2 and with saturated NaCl solution and dried over $Na_2SO_4$ and the solvent is evaporated under vacuum. This gives 12 g of the expected product, which is used as it is.

B) 4-(4-Chlorophenyl)-4-piperidinecarbonitrile hydrochloride.

A mixture of 18 g of the compound obtained in the preceding step in 100 ml of MeOH and 20 ml of concentrated HCl solution is heated at 40-50° C. for 3 hours. The reaction mixture is concentrated under vacuum, the residue is taken up twice in MeOH and each time the solvent is evaporated under vacuum. This gives 5.85 g of the expected product following recrystallization from acetone.

Preparation 1.13

4-(3-Methylphenyl)-4-piperidinol (IV): $R_1$=3-$CH_3$; $R_2$=H; $R_3$=—OH.

A) 1-Benzyl-4-(3-methylphenyl)-4-piperidinol.

This compound is prepared by the procedure described in step A of preparation 1.7, from 1.55 g of magnesium in 25 ml of THF, a solution of 11 g of 3-bromotoluene in 15 ml of THF and a solution of 10 g of 1-benzyl-4-piperidone in 30 ml of THF. The product obtained is chromatographed on silica gel, eluting with a DCM/MeOH (97/3; v/v) mixture. This gives 14.5 g of the expected product.

B) 4-(3-Methylphenyl)-4-piperidinol.

A mixture of 14.5 g of the compound obtained in the preceding step and 2 g of 10% palladium on carbon in 500 ml of MeOH is hydrogenated at 25° C. under atmospheric pressure for 48 hours. The catalyst is filtered off and the filtrate is concentrated under vacuum. This gives 8.9 g of the expected product.

Preparation 1.14

4-(3-Methoxyphenyl)-4-piperidinol (IV): $R_1$=3-$OCH_3$; $R_2$=H; $R_3$=—OH.

A) 1-Benzyl-4-(3-methoxyphenyl)-4-piperidinol.

This compound is prepared by the procedure described in step A of preparation 1.7, from 1.55 g of magnesium in 25 ml of THF, a solution of 12 g of 3-bromoanisole and 15 ml of THF and a solution of 10 g of 1-benzyl-4-piperidone in 30 ml of THF. The product obtained is chromatographed on silica gel, eluting with a DCM/MeOH (97/3 to 95/5; v/v) mixture. This gives 13.7 g of the expected product.

B) 4-(3-Methoxyphenyl)-4-piperidinol.

A mixture of 13.7 g of the compound obtained in the preceding step and 2 g of 10% palladium on carbon in 500 ml of EtOH is hydrogenated at 25° C. under atmospheric pressure for 48 hours. The catalyst is filtered off and the filtrate is concentrated under vacuum. This gives 10.8 g of the expected product.

Preparation 1.15

N-[4-[4-Chloro-3-(trifluoromethyl)phenyl]-4-piperidyl]acetamide hydrochloride (IV), HCl: $R_1$=3-$CF_3$; $R_2$=4-Cl; $R_3$=—NHCOCH$_3$.

A) 1-Benzyl-4-[4-chloro-3-(trifluoromethyl)phenyl]-4-piperidinol.

A mixture of 15 g of 4-[4-chloro-3-(trifluoromethyl)phenyl]-4-piperidinol, 8.3 g of $K_2CO_3$ and 7.18 ml of benzyl bromide in 80 ml of DMF is left with stirring at AT for 2 days. The reaction mixture is poured into water and extracted with AcOEt, an insoluble product is filtered off, the organic phase is washed with water and with saturated NaCl solution and dried over $Na_2SO_4$ and the solvent is evaporated under vacuum. The residue is chromatographed on silica gel, eluting with a DCM/MeOH (95/5; v/v) mixture. This gives 14.6 g of the expected product.

B) N-[1-Benzyl-4-[4-chloro-3-(trifluoromethyl)-phenyl]-4-piperidyl]acetamide.

An ice bath is used to cool 30 ml of concentrated $H_2SO_4$, a solution of 7.98 g of the compound obtained in the preceding step in 60 ml of acetonitrile is added dropwise at a temperature of less than 15° C. and the mixture is left with stirring at 15° C. for 2 days. The reaction mixture is poured onto ice, rendered alkaline by addition of NaOH pellets and extracted with AcOEt, the organic phase is dried over Na$_2$SO$_4$ and the solvent is evaporated under vacuum to give an impure solid (7.86 g). The residue is chromatographed on silica gel, eluting with a DCM/MeOH (97/3 to 95/5; v/v) mixture. This gives 4.26 g of the expected product following recrystallization from a DCM/iso ether mixture; m.p.=198-199° C.

C) N-[4-[4-Chloro-3-(trifluoromethyl)phenyl]-4-piperidyl] acetamide hydrochloride.

A mixture of 3.1 g of the compound obtained in the preceding step, and 1.05 g of K$_2$CO$_3$ in 25 ml of DCM is left with stirring at AT for 15 minutes, then cooled with an ice bath, admixed dropwise with a solution of 1.2 ml of 1-chloroethyl chloroformate in 5 ml of DCM and left with stirring at 4° C. for 2 hours. An insoluble product is filtered off, the filtrate is concentrated under vacuum, the residue is taken up in MeOH and the solvent is evaporated under vacuum. The residue is taken up with 80 ml of MeOH and heated at reflux for 15 minutes and the solvent is evaporated under vacuum. This gives 2.7 g of the expected product.

D) tert-Butyl 4-(acetylamino)-4-[4-chloro-3-(trifluoromethyl)phenyl]-1-piperidinecarboxylate.

A mixture of 2.7 g of the compound obtained in the preceding step, 1.9 ml of DIPEA and 1.64 g of di-tert-butyl dicarbonate in 20 ml of DCM is left with stirring at AT for 2 hours. The mixture is concentrated under vacuum and the residue is chromatographed on silica gel, eluting with a DCM/MeOH (98/2; v/v) mixture. This gives 1.4 g of the expected product.

E) N-[4-[4-chloro-3-(trifluoromethyl)phenyl]-4-piperidyl] acetamide hydrochloride.

A suspension of 1.4 g of the compound obtained in the preceding step in 20 ml of dioxane is admixed with 4 ml of 2N hydrochloric ether solution and left with stirring at AT for 2 hours. The reaction mixture is concentrated under vacuum to give the expected product, which is used as it is.

Preparation 1.16

4-[3-(Trifluoromethoxy)phenyl]-4-piperidinol hydrochloride (IV), HCl: R$_1$=3-OCF$_3$; R$_2$=H; R$_3$=—OH A) 1-Benzyl-4-[3-(trifluoromethoxy)phenyl]-4-piperidinol hydrochloride This compound is prepared by the procedure described in step A of preparation 1.7, from 2 g of magnesium in 25 ml of THF, a solution of 20 g of 1-bromo-3-(trifluoromethoxy) benzene in 15 ml of THF and a solution of 13 g of 1-benzyl-4-piperidone in 30 ml of THF. The hydrochloride of the product obtained is formed in 2N hydrochloric ether solution. This gives 24.4 g of the expected product.

B) 4-[3-(trifluoromethoxy)phenyl]-4-piperidinol hydrochloride

A mixture of 24 g of the compound obtained in the preceding step, 16 g of ammonium formate and 2 g of 10% palladium on carbon in 500 ml of MeOH is left with stirring at AT for 4 hours. The catalyst is filtered off and the filtrate is concentrated under vacuum. The residue is taken up with saturated K$_2$CO$_3$ solution and extracted with ether, the organic phase is washed with saturated NaCl solution and dried over Na$_2$SO$_4$ and the solvent is evaporated under vacuum. The residue is taken up with 2N hydrochloric ether solution and the precipitate formed is isolated with suction. This gives 6.2 g of the expected product, m.p.=145-146° C.

Preparation 1.17 tert-Butylmethyl [[4-[3-(trifluoromethyl)-phenyl] piperidin-4-yl]methyl]carbamate (IV): R$_1$=3-CF$_3$; R$_2$=H; R$_3$=—CH$_2$N(CH$_3$)—COOC(CH$_3$)$_3$ A) N,N-Bis(2-chloroethyl)benzylamine.

An ice bath is used to cool a mixture of 150 g of N,N-bis(2-chloroethyl)amine hydrochloride and 100 ml of benzyl bromide in 1 000 ml of DMF and then 120 ml of triethylamine are added dropwise and the mixture is left with stirring at AT overnight. The reaction mixture is concentrated under vacuum, the residue is taken up in water and extracted 3 times with ether, the organic phases are dried over Na$_2$SO$_4$ and the solvent is evaporated under vacuum. This gives 113 g of the expected product.

B) 1-Benzyl-4-[3-(trifluoromethyl)phenyl]-4-piperidinecarbonitrile hydrochloride.

A suspension of 23.24 g of sodium hydride at a concentration of 60% in oil in 100 ml of DMSO and 100 ml of THF is admixed dropwise under an inert atmosphere and at AT with a solution of 50 g of 3-(trifluoromethyl)phenylacetonitrile in 150 ml of DMSO and the mixture is left with stirring for 15 minutes. A solution of 62.43 g of the compound obtained in the preceding step in 150 ml of DMSO is subsequently added over 1 hour and the mixture is left with stirring at AT overnight. An ice/water mixture is added, the system is extracted with ether, the organic phase is dried over Na$_2$SO$_4$ and the solvent is evaporated under vacuum. The residue is taken up in 1000 ml of hot EtOH, the system is left with stirring at AT for 48 hours and the crystalline product formed is isolated with suction. This gives 50 g of the expected product.

C) [1-Benzyl-4-[3-(trifluoromethyl)phenyl]-4-piperidyl] methylamine.

30 g of the compound obtained in the preceding step are dissolved in 10% NaOH solution and extracted with ether, the organic phase is dried over Na$_2$SO$_4$ and the solvent is evaporated under vacuum. The product, in the form of the free base, is taken up in 500 ml of MeOH and 30 ml of 20% aqueous ammonia solution, 3 g of Raney® nickel are added and the system is hydrogenated at AT under atmospheric pressure overnight. The catalyst is filtered off and the filtrate is concentrated under vacuum. The residue is taken up in water and extracted with AcOEt, the organic phase is dried over Na$_2$SO$_4$ and the solvent is evaporated under vacuum. This gives 27 g of the expected product.

D) [[1-Benzyl-4-[3-(trifluoromethyl)phenyl]-4-piperidyl] methyl]formamide.

A mixture of 27 g of the compound obtained in the preceding step and 300 ml of ethyl formate is left with stirring at AT overnight, then heated at 60° C. for 6 hours and left with stirring at AT for 48 hours. It is concentrated under vacuum, the residue is taken up with 10% HCl solution, the acidic aqueous phase is washed with ether, ice is added and the mixture is rendered alkaline by addition of 10% NaOH solution and extracted with ether, the organic phase is dried over Na$_2$SO$_4$ and the solvent is evaporated under vacuum. The residue is chromatographed on silica gel H, eluting with DCM and then with a DCM/MeOH (100/4; v/v) mixture. This gives 20 g of the expected product.

E) [[1-Benzyl-4-[3-(trifluoromethyl)phenyl]-4-piperidyl] methyl]methylamine.

A suspension of 4 g of lithium aluminium hydride in 400 ml of ether is admixed at AT with 20 g of the compound obtained in the preceding step and then left with stirring at AT for 16 hours. Subsequently, in succession, 3 ml of water, 3 ml of 30% NaOH and 1 ml of water are added and the mixture is left with stirring. The mineral salts are filtered off on Celite, the filtrate is decanted, the organic phase is dried over Na$_2$SO$_4$ and the solvent is evaporated under vacuum. This gives 18 g of the expected product.

F) tert-Butyl [[1-benzyl-4-[3-(trifluoromethyl)-phenyl]-4-piperidyl]methyl]methylcarbamate.

A mixture of 18 g of the compound obtained in the preceding step and 9.6 g of di-tert-butyl dicarbonate in 300 ml of DCM is left with stirring at AT for 1 hour. Water is added to the reaction mixture, which is then extracted with DCM, the organic phase is dried over Na$_2$SO$_4$ and the solvent is evaporated under vacuum. The residue is chromatographed on silica gel H, eluting with a DCM/MeOH (100/2; v/v) mixture. This gives 21 g of the expected product.

G) tert-Butylmethyl [4-[3-(trifluoromethyl)phenyl]-piperidin-4-yl]methyl]carbamate.

A mixture of 21 g of the compound obtained in the preceding step in 2 g of 10% palladium on carbon in 300 ml of MeOH is hydrogenated at AT under atmospheric pressure for 12 hours. The catalyst is filtered off and the filtrate is concentrated under vacuum. This gives 16 g of the expected product.

Preparation 1.18

4-(3-Chlorophenyl)-4-piperidinecarbonitrile hydrochloride (IVa), HCl: R$_1$=3-Cl; R$_2$=H A) tert-Butyl-4-(3-chlorophenyl)-4-cyanopiperidine-1-carboxylate.

A suspension of 15.8 g of sodium hydride of a concentration of 60% in oil in 400 ml of DMSO is admixed dropwise at AT under an inert atmosphere with a solution of 30 g of 3-chlorophenylacetonitrile in 200 ml of THF and then with a solution of 45.5 g of tert-butyl bis(2-chloroethyl) carbamate in 200 ml of DMSO and is heated at 60° C. overnight. The reaction mixture is poured into an ice/water mixture and extracted with ether, the organic phase is washed with water and dried over Na$_2$SO$_4$ and the solvent is evaporated under vacuum. The residue is chromatographed on silica gel, eluting with DCM. This gives 33 g of the expected product.

B) 4-(3-Chlorophenyl)-4-piperidinecarbonitrile hydrochloride.

A mixture of 6.7 g of the compound obtained in the preceding step, 100 ml of 2N hydrochloric ether solution and 20 ml of MeOH is left with stirring at AT for 3 hours. It is concentrated under vacuum, the residue is taken up in ether and the precipitate formed is isolated with suction. This gives 4.65 g of the expected product, m.p.=198° C.

Preparation 1.19

4-(3-methoxyphenyl)-4-piperidinecarbonitrile hydrochloride (IVa), HCl: R$_1$=3-OCH$_3$; R$_2$=H A) tert-Butyl 4-(3-methoxyphenyl)-4-cyanopiperidine-1-carboxylate.

This compound is prepared by the procedure described in step A of preparation 1.8, from 16.3 g of sodium hydride at a concentration of 60% in oil in 400 ml of DMSO, 30 g of 3-methoxyphenylacetonitrile in 150 ml of THF and 47 g of tert-butyl bis(2-chloroethyl)carbamate in 100 ml of DMSO. This gives 54 g of the expected product.

B) 4-(3-Methoxyphenyl)-4-piperidinecarbonitrile hydrochloride.

A mixture of 48 g of the compound obtained in the preceding step, 300 ml of 2N hydrochloric ether solution and 50 ml of MeOH is left with stirring at AT for 2 hours. The precipitate formed is isolated with suction to give 30.5 g of the expected product, m.p.=172° C.

Preparation 1.20

4-(Azetidin-1-ylcarbonyl)-4-[3-(trifluoromethyl) phenyl]piperidine (IV):

R$_1$ = 3-CF$_3$;

R$_2$ = H;

R$_3$ = —CO—N.

A) 4-(Chloroformyl)-4-[3-(trifluoromethyl)phenyl]piperidine hydrochloride.

A mixture of 1 g of the compound obtained in step A of preparation 1.9 and 10 ml of thionyl chloride in 10 ml of DCM is heated at 60° C. for 2 hours. It is concentrated under vacuum to give 1.05 g of the expected product, which is used as it is.

B) 4-(Azetidin-1-ylcarbonyl)-1-benzyl-4-[3-(trifluoromethyl)phenyl]piperidine.

A mixture of 1.05 g of the compound obtained in the preceding step, 0.283 g of azetidine and 1.15 ml of triethylamine in 10 ml of DCM is left with stirring at AT overnight. Saturated K$_2$CO$_3$ solution is added to the reaction mixture, which is then extracted with DCM, the extract is dried over Na$_2$SO$_4$ and the solvent is evaporated under vacuum. The residue is chromatographed on silica gel, eluting with a DCM/MeOH (97/3; v/v) mixture. This gives 0.43 g of the expected product.

C) 4-(Azetidin-1-ylcarbonyl)-4-[3-(trifluoromethyl)-phenyl]piperidine.

A mixture of 0.43 g of the compound obtained in the preceding step, 1 g of 10% palladium on carbon and 20 ml of MeOH is hydrogenated at 25° C. under atmospheric pressure overnight. The catalyst is filtered off and the filtrate is concentrated under vacuum. This gives 0.33 g of the expected product, which is used as it is.

2. Preparations of Compounds of Formula (II)

Preparation 2.1

2-Chloro-1-[4-[3-(trifluoromethyl)phenyl]-1-piperidyl]-1-ethanone (IIa): $R_1$=3-$CF_3$; $R_2$=H; $R_3$=H; Hal=Cl.

An ice bath is used to cool a mixture of 2.5 g of 4-[3-(trifluoromethyl)phenyl]piperidine and 4 ml of triethylamine in 30 ml of DCM, which is then admixed dropwise with 0.85 ml of 2-chloroacetyl chloride and left with stirring for 3 hours, during which the temperature is allowed to return to AT. It is concentrated under vacuum, the residue is taken up with aqueous 1N HCl solution and extracted with AcOEt, the organic phase is washed with saturated NaCl solution and dried over $Na_2SO_4$ and the solvent is evaporated under vacuum. This gives 3.1 g of the expected product, which is used as it is.

Preparation 2.2

2-Chloro-1-[4-hydroxy-4-[3-(trifluoromethyl)phenyl]-1-piperidyl]-1-ethanone (IIa): $R_1$=3-$CF_3$; $R_2$=H; $R_3$=—OH; Hal=Cl.

A mixture of 5 g of the compound obtained in preparation 1.1 and 10 ml of DIPEA in 40 ml of DCM is admixed dropwise and at AT with 1.63 ml of 2-chloroacetyl chloride and left with stirring for 30 minutes. The reaction mixture is washed with water, the organic phase is dried over $Na_2SO_4$ and the solvent is evaporated under vacuum. The residue is chromatographed on silica gel, eluting with a DCM/MeOH (97/3; v/v) mixture. This gives 5.5 g of the expected product, which is used as it is.

Preparation 2.3

1-[4-Hydroxy-4-[3-(trifluoromethyl)phenyl]-1-piperidyl]-2-propen-1-one (IIb): $R_1$=3-$CF_3$; $R_2$=H; $R_3$=—OH.

An ice bath is used to cool a mixture of 5 g of the compound obtained in preparation 1.1 and 8 ml of triethylamine in 50 ml of DCM which is then admixed dropwise with 2.07 ml of 3-bromopropionyl chloride and left with stirring for 2 hours, during which the temperature is allowed to return to AT. The reaction mixture is washed with saturated $K_2CO_3$ solution and with water, the organic phase is dried over $Na_2SO_4$ and the solvent is evaporated under vacuum. The residue is chromatographed on silica gel, eluting with a DCM/MeOH (98.5/1.5 to 97/3; v/v) mixture. This gives 4.6 g of the expected product, which is used as it is.

Preparation 2.4

2-Chloro-1-[4-methoxy-4-[3-(trifluoromethyl)-phenyl]-1-piperidyl]-1-ethanone (IIa): $R_1$=3-$CF_3$; $R_2$=H; $R_3$=—$OCH_3$; Hal=Cl.

A mixture of 1 g of the compound obtained in preparation 1.2 and 1.4 ml of triethylamine in 20 ml of DCM is admixed dropwise and at AT with 0.3 ml of 2-chloroacetyl chloride and left with stirring at AT for 3 hours. It is concentrated under vacuum, the residue is taken up with aqueous 1N HCl solution and extracted with AcOEt, the organic phase is washed with NaCl solution and dried over $Na_2SO_4$ and the solvent is evaporated under vacuum. This gives 1.2 g of the expected product, which is used as it is.

Preparation 2.5

2-Chloro-1-[4-(dimethylamino)-4-[3-(trifluoromethyl)phenyl]-1-piperidyl]-1-ethanone (IIa): $R_1$=3-$CF_3$; $R_2$=H; $R_3$=—$N(CH_3)_2$; Hal=Cl.

An ice bath is used to cool a mixture of 1 g of the compound obtained in preparation 1.3 and 1 ml of triethylamine in 20 ml of DCM which is then admixed dropwise with 0.35 ml of 2-chloroacetyl chloride and left with stirring, during which the temperature is allowed to return to AT. It is concentrated under vacuum, the residue is extracted with AcOEt, the organic phase is washed with saturated $K_2CO_3$ solution and dried over $Na_2SO_4$ and the mixture is evaporated under vacuum. This gives 1.4 g of the expected product, which is used as it is.

Preparation 2.6

1-(2-Chloroacetyl)-4-[3-(trifluoromethyl)-phenyl]-4-piperidinecarbonitrile (IIc): $R_1$=3-$CF_3$; $R_2$=H; Hal=Cl.

A mixture of 4.8 g of the compound obtained in preparation 1.4, free base, and 2.7 ml of triethylamine in 50 ml of DCM is admixed dropwise and at AT with 1.5 ml of 2-chloroacetyl chloride and is left with stirring at AT for 1 hour. 10% HCl solution is added to the reaction mixture, which is then decanted, the organic phase is washed with 10% NaOH solution and dried over $Na_2SO_4$ and the solvent is evaporated under vacuum. This gives 3.42 g of the expected product following recrystallization from ether; m.p.=120° C.

Preparation 2.7 tert-Butyl [1-(2-chloroacetyl)-4-[3-(trifluoromethyl)phenyl]-4-piperidyl]methylcarbamate (IIa): $R_1$=3-$CF_3$; $R_2$=H; $R_3$=—$CH_2NHCOOC(CH_3)_3$, Hal=Cl.

An ice bath is used to cool a mixture of 4.95 g of the compound obtained in preparation 1.5 and 6.8 ml of triethylamine in 50 ml of DCM which is then admixed dropwise with 1.65 ml of 2-chloroacetyl chloride and left with stirring, during which the temperature is allowed to return to AT. It is concentrated under vacuum, the residue is taken up with saturated $K_2CO_3$ solution and extracted with AcOEt, the organic phase is washed with saturated $K_2CO_3$ solution, with buffer solution pH=2 and with saturated NaCl solution and dried over $Na_2SO_4$ and the mixture is evaporated under vacuum. The residue is chromatographed on silica gel, eluting with DCM/AcOEt (80/20; v/v) mixture. This gives 1.8 g of the expected product, which is used as it is.

Preparation 2.8

1-(2-Chloroacetyl)-4-[3-(trifluoromethyl)-phenyl]-4-piperidinecarboxamide (IIa): $R_1$=3-$CF_3$; $R_2$=H; $R_3$=—$CONH_2$; Hal=Cl.

A mixture of 0.7 g of the compound obtained in preparation 1.6 and 0.37 ml of triethylamine in 10 ml of DCM and 10 ml of dioxane is admixed dropwise and at AT with 0.21 ml of 2-chloroacetyl chloride and is left with stirring at AT for 2 hours. It is concentrated under vacuum, the residue is taken up in water, and the precipitate formed is isolated with suction and dried. This gives 0.82 g of the expected product, m.p.=195-198° C.

Preparation 2.9

2-Chloro-1-[4-hydroxy-4-[2-(trifluoromethyl)-phenyl]-1-piperidyl]-1-ethanone (IIa): $R_1$=2-$CF_3$; $R_2$=H; $R_3$=—OH; Hal=Cl.

An ice bath is used to cool a mixture of 1.8 g of the compound obtained in preparation 1.7 and 1 ml of triethylamine in 20 ml of DCM which is then admixed dropwise with 0.65 ml of 2-chloroacetyl chloride and left with stirring for 1 hour, during which the temperature is allowed to return to AT. Water is added to the reaction mixture, which is concentrated under vacuum to remove the DCM and subjected to extraction with AcOEt, the organic phase is washed with water and with saturated NaCl solution and dried over $Na_2SO_4$ and the solvent is evaporated under vacuum. This gives 1.8 g of the expected product, which is used as it is.

Preparation 2.10

1-(2-Chloroacetyl)-4-[2-(trifluoromethyl)-phenyl]-4-piperidinecarbonitrile (IIc): $R_1$=2-$CF_3$; $R_2$=H; Hal=Cl.

A mixture of 2.1 g of the compound obtained in preparation 1.8 and 2 ml of triethylamine in 20 ml of DCM is admixed at AT with 0.6 ml of 2-chloroacetyl chloride and left with stirring for 30 minutes. It is concentrated under vacuum, and the residue is taken up with 10% HCl solution and extracted with AcOEt, the organic phase is washed with water, with saturated $K_2CO_3$ solution and with saturated NaCl solution and dried over $Na_2SO_4$ and the solvent is evaporated under vacuum. This gives 2.3 g of the expected product.

Preparation 2.11

[1-(2-Chloroacetyl)-4-[3-(trifluoromethyl)-phenyl]-4-piperidyl]methyl acetate (IIa): $R_1$=3-$CF_3$; $R_2$=H; $R_3$=—$CH_2OCOCH_3$; Hal=Cl.

A mixture of 1 g of the compound obtained in preparation 1.10 and 0.46 ml of triethylamine in 20 ml of DCM is cooled to 0° C., 0.27 ml of 2-chloroacetyl chloride is added and the mixture is left with stirring at 0° C. for 30 minutes. Water is added to the reaction mixture, which is extracted with DCM, the organic phase is dried over $Na_2SO_4$ and the solvent is evaporated under vacuum. This gives 0.9 g of the expected product.

Preparation 2.12

2-Chloro-1-[4-hydroxy-4-[4-(trifluoromethyl)-phenyl]-1-piperidyl]-1-ethanone (IIa): $R_1$=4-$CF_3$; $R_2$=H; $R_3$=—OH; Hal=Cl.

An ice bath is used to cool a mixture of 1.2 g of the compound obtained in preparation 1.11 and 1.2 ml of triethylamine in 20 ml of DCM which is then admixed dropwise with 0.38 ml of 2-chloroacetyl chloride and left with stirring for 1 hour, during which the temperature is allowed to return to AT. Water is added to the reaction mixture, which is extracted with DCM, the organic phase is dried over $Na_2SO_4$ and the solvent is evaporated under vacuum. This gives 1.36 g of the expected product, which is used as it is.

Preparation 2.13

2-Chloro-1-[4-(4-chlorophenyl)-4-hydroxy-1-piperidyl]-1-ethanone (IIa): $R_1$=4-Cl; $R_2$=H; $R_3$=—OH; Hal=Cl.

This compound is prepared by the procedure described in preparation 2.12, from 4-(4-chlorophenyl)-4-piperidinol (available commercially) and 2-chloroacetyl chloride.

Preparation 2.14

1-(2-Chloroacetyl)-4-(4-chlorophenyl)-4-piperidinecarbonitrile (IIc): $R_1$=4-Cl; $R_2$=H; Hal=Cl.

This compound is prepared by the procedure described in preparation 2.1, from the compound obtained in preparation 1.12 and 2-chloroacetyl chloride.

Preparation 2.15

2-Chloro-1-[4-hydroxy-4-(3-methylphenyl)-1-piperidyl]-1-ethanone (IIa): $R_1$=3-$CH_3$; $R_2$=H; $R_3$=—OH; Hal=Cl.

This compound is prepared by the procedure described in preparation 2.1, from the compound obtained in preparation 1.13 and 2-chloroacetyl chloride.

Preparation 2.16

2-Chloro-1-[4-hydroxy-4-(3-methoxyphenyl)-1-piperidyl]-1-ethanone (IIa): $R_1$=3-$OCH_3$; $R_2$=H; $R_3$=—OH; Hal=Cl.

This compound is prepared by the procedure described in preparation 2.1, from the compound obtained in preparation 1.14 and 2-chloroacetyl chloride.

Preparation 2.17

2-Chloro-1-[4-[4-chloro-3-(trifluoromethyl)-phenyl]-4-hydroxy-1-piperidyl]-1-ethanone (IIa): $R_1$=3-$CF_3$; $R_2$=4-Cl; $R_3$=—OH; Hal=Cl.

This compound is prepared by the procedure described in preparation 2.1, from 4-[4-chloro-3-(trifluoromethyl)phenyl]-4-piperidinol and 2-chloroacetyl chloride.

Preparation 2.18

N-[1-(2-Chloroacetyl)-4-[4-chloro-3-(trifluoromethyl)phenyl]-4-piperidyl]acetamide (IIa): $R_1$=3-$CF_3$; $R_2$=4-Cl; $R_3$=—NHCOCH$_3$; Hal=Cl.

This compound is prepared by the procedure described in preparation 2.2, from the compound obtained in preparation 1.15 and 2-chloroacetyl chloride.

Preparation 2.19

2-Chloro-1-[4-hydroxy-4-[3-(trifluoromethoxy)phenyl]-1-piperidyl]-1-ethanone.

(IIa): $R_1$=3-OCF$_3$; $R_2$=H; $R_3$=—OH; Hal=Cl.

This compound is prepared by the procedure described in preparation 2.1, from the compound obtained in preparation 1.16 and 2-chloroacetyl chloride.

Preparation 2.20 tert-Butyl [[1-(2-chloroacetyl)-4-[3-(trifluoromethyl)phenyl]-4-piperidyl]methyl]-methylcarbamate (IIa): $R_1$=3-CF$_3$; $R_2$=H; $R_3$=—CH$_2$N(CH$_3$)COOC(CH$_3$)$_3$; Hal=Cl.

A solution of 14 g of the compound obtained in preparation 1.17 and 5.5 ml of triethylamine in 300 ml of DCM is cooled to −40° C., 3.1 ml of 2-chloroacetyl chloride are added slowly and the mixture is left with stirring, during which the temperature is allowed to return to AT. It is concentrated under vacuum, the residue is taken up in water and extracted with AcOEt, the organic phase is washed with buffer pH=2 and water and dried over Na$_2$SO$_4$ and the solvent is evaporated under vacuum. This gives 15.33 g of the expected product.

Preparation 2.21

1-(2-Chloroacetyl)-4-(3-chlorophenyl)-4-piperidinecarbonitrile (IIc): $R_1$=3-Cl; $R_2$=H; Hal=Cl.

This compound is prepared by the procedure described in preparation 2.1, from the compound obtained in preparation 1.18 and 2-chloroacetyl chloride.

Preparation 2.22

1-(2-Chloroacetyl)-4-(3-methoxyphenyl)-4-piperidinecarbonitrile (IIc): $R_1$=3-OCH$_3$; $R_2$=H; Hal=Cl.

This compound is prepared by the procedure described in preparation 2.1, from the compound obtained in preparation 1.19 and 2-chloroacetyl chloride.

Preparation 2.23

4-(Azetidin-1-ylcarbonyl)-1-(2-chloroacetyl)-4-[3-(trifluoromethyl)phenyl]piperidine (IIa):

$R_1$ = 3-CF$_3$;

$R_2$ = H;

$R_3$ = 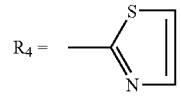 ; Hal = Cl

This compound is prepared by the procedure described in preparation 2.1, from the compound obtained in preparation 1.20 and 2-chloroacetyl chloride.

Preparation 3.1

1-(1,3-Thiazol-2-yl)piperazine dihydrochloride (III), 2HCl;

$R_4$ = 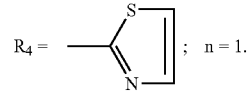

A) tert-Butyl 4-(1,3-thiazol-2-yl)-1-piperazinecarboxylate

A mixture of 5 g of tert-butyl 1-piperazinecarboxylate, 4.4 g of 2-bromo-1,3-thiazole and 7.4 g of K$_2$CO$_3$ in 50 ml of EtOH is heated at reflux for 4 days. Water is added to the reaction mixture, the EtOH is evaporated under vacuum, the resulting aqueous phase is extracted with AcOEt, the organic phase is washed with saturated K$_2$CO$_3$ solution and with saturated NaCl solution and dried over Na$_2$SO$_4$ and the solvent is evaporated under vacuum. The residue is chromatographed on silica gel, eluting with a DCM/MeOH (98/2; v/v) mixture. This gives 5 g of the expected product following cold precipitation from a DCM/hexane mixture and isolation with suction; m.p.=114-116° C.

B) 1-(1,3-thiazol-2-yl)piperazine dihydrochloride.

A mixture of 2.8 g of the compound obtained in the preceding step and 50 ml of a 2 N solution of HCl in ether is left with stirring at AT for 7 hours, a minimum amount of DCM and then of MeOH having been added beforehand until the reaction mixture dissolves. The mixture is concentrated under vacuum to give 2.35 g of the expected product, which is used as it is.

EXAMPLE 1

Compound No. 1

1-[4-hydroxy-4-(3-(trifluoromethyl)phenyl]-1-piperidyl]-2-[4-(1,3-thiazol-2-yl)-1-piperazinyl]-1-ethanone (I):

$R_1$ = 3-CF$_3$;

$R_2$ = H;

$R_3$ = —OH;

$R_4$ = 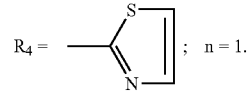 ; n = 1.

A mixture of 0.5 g of the compound obtained in preparation 2.2, 0.376 g of the compound obtained in preparation 3.1, 0.297 g of potassium iodide and 1.15 g of $K_2CO_3$ in 30 ml of acetonitrile is left with stirring at AT for 2 hours. A 5% $K_2CO_3$ solution is added to the reaction mixture, which is extracted with AcOEt, the organic phase is washed with water and with saturated NaCl solution and dried over $Na_2SO_4$ and the solvent is evaporated under vacuum. The residue is chromatographed on silica gel, eluting with a DCM/MeOH (95/5; v/v) mixture. This gives 0.5 g of the expected product following recrystallization from a DCM/iso ether mixture; m.p.=157-158° C.

EXAMPLE 2

Compound No. 2

2-[4-(1,3-Thiazol-2-yl)-1-piperazinyl]-1-[4-[3-(trifluoromethyl)phenyl]-3,6-dihydro-1-(2H)-pyridyl]-1-ethanone dioxalate (I), $2C_2H_2O_4$:

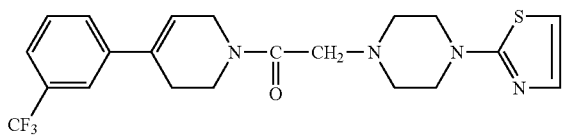

A mixture of 0.35 g of compound No. 1 obtained in example 1, 3 ml of a 35% HCl solution and 6 ml of acetic acid is heated at 100° C. for 1 hour. A 5% $K_2CO_3$ solution is added to the reaction mixture, which is extracted with AcOEt, the organic phase is washed with water and dried over $Na_2SO_4$ and the solvent is evaporated under vacuum. The residue is chromatographed on silica gel, eluting with a DCM/MeOH (97/3; v/v) mixture. 0.21 g of the product obtained is taken up in ether, 0.086 g of oxalic acid is added, trituration is carried out and the precipitate formed is isolated with suction. This gives 0.254 g of the expected product, m.p.=132-133° C.

EXAMPLE 3

Compound No. 3

1-[4-(Aminomethyl)-4-[3-(trifluoromethyl)-phenyl]-1-piperidyl]-2-[4-(1,3-thiazol-2-yl)-1-piperazinyl]-1-ethanone trihydrochloride (I), 3HCl:

$R_1$ = 3-$CF_3$;

$R_2$ = H;

$R_3$ = —$CH_2NH_2$;

$R_4$ = 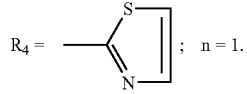 ; n = 1.

A) 1-[2-[4-(1,3-Thiazol-2-yl)-1-piperazinyl)acetyl]-4-[3-(trifluoromethyl)phenyl-4-piperidinecarbonitrile.

A mixture of 0.7 g of the compound obtained in preparation 2.6, 0.44 g of the compound obtained in preparation 3.1, 0.58 g of $K_2CO_3$ and 0.35 g of KI in 20 ml of acetonitrile is left with stirring at AT overnight. It is concentrated under vacuum, the residue is taken up in water and extracted with AcOEt, the organic phase is dried over $Na_2SO_4$ and the solvent is evaporated under vacuum. The residue is chromatographed on silica gel, eluting with DCM and then with a DCM/MeOH (100/2; v/v) mixture. This gives 0.57 g of the expected product.

B) 1-[4-(Aminomethyl)-4-[3-(trifluoromethyl)phenyl]-1-piperidyl]-2-[4-(1,3,thiazol-2-yl)-1-piperazinyl]-1-ethanone trihydrochloride.

A mixture of 0.57 g of the compound obtained in the preceding step, 0.05 g of Raney® nickel, 5 ml of a 20% aqueous ammonia solution and 20 ml of MeOH is hydrogenated at AT under atmospheric pressure overnight. The catalyst is filtered and the filtrate is concentrated under vacuum. The residue is taken up in water and extracted with AcOEt, the organic phase is dried over $Na_2SO_4$ and the solvent is evaporated under vacuum. The residue is chromatographed on silica gel H, eluting with a DCM/MeOH (100/2; v/v) mixture and then with a DCM/MeOH/$H_2O$ (100/5/0.5; v/v/v) mixture. The residue is taken up with a 2 N solution of HCl in ether, which is concentrated under vacuum, the residue is taken up in acetone and the precipitate formed is isolated with suction. This gives 0.05 g of the expected product, m.p.>232° C.

Mass spectrum: $MH^+$=468.4. $^1H$ NMR: 250 MHz: DMSO-$d_6$: δ (ppm): 1.8 to 2.4: mt: 4H; 2.9 to 4.2: unres. comp.: 14H; 4.4: sd: 2H; 4.6 to 5.7: exchangeable unres. comp.: exchangeable H; 7.0: d: 1H; 7.3: d: 1H; 7.6 to 7.9: unres. comp.: 4H; 8.0: bs: 3H exchangeable.

EXAMPLE 4

Compound No. 9

1-[4-[(Dimethylamino)methyl]-4-[3-(trifluoromethyl)phenyl]-1-piperidyl]-2-[4-(1,3-thiazol-2-yl)-1-piperazinyl]-1-ethanone (I):

$R_1$ = 3-$CF_3$;

$R_2$ = H;

$R_3$ = —$CH_2N(CH_3)_2$;

$R_4$ = 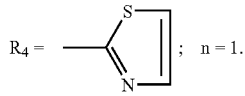 ; n = 1.

A solution of 0.65 g of compound No. 3 and 10 ml of THF is admixed with 0.5 ml of acetic acid and then, at AT, over 5 hours and in portions, with 1 ml of 37% aqueous formaldehyde solution and with 2.38 g of sodium triacetoxyborohydride and the mixture is left with stirring at AT overnight. 50 ml of MeOH are added and the mixture is heated at 80° C. for 1 hour 30 minutes. It is concentrated under vacuum, the residue is taken up with 5% $K_2CO_3$ solution and extracted with AcOEt, the organic phase is washed with water and with saturated NaCl solution and dried over $Na_2SO_4$ and the solvent is evaporated under vacuum. The residue is chromatographed on silica gel, eluting with a DCM/MeOH (92/8; v/v) mixture. This gives 0.16 g of the expected product in the form of a thick oil.

$^1$H NMR: DMSO-$d_6$: δ (ppm): 1.7: mt: 2H; 1.9: s: 6H; 2.1: mt: 2H; 2.4: s: 2H; 2.5: unres. comp.: 4H; 2.9: mt: 1H; 3.0 to 3.5: unres. comp.: 7H; 3.8: mt: 2H; 6.8: d: 1H; 7.1: d: 1H; 7.5 to 7.8: unres. comp.: 4H.

EXAMPLE 5

Compound No. 10

1-[4-[(Methylamino)methyl]-4-[3-(trifluoromethyl) phenyl]-1-piperidyl]-2-[4-(1,3-thiazol-2-yl)-1-piperazinyl]-1-ethanone (I):

$R_1$ = 3-$CF_3$;

$R_2$ = H;

$R_3$ = —$CH_2NHCH_3$;

$R_4$ = 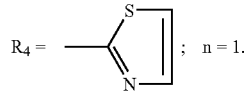 ; n = 1.

A) tert-Butyl methyl [[1-[2-[4-(1,3-thiazol-2-yl)-1-piperazinyl]acetyl]-4-[3-(trifluoromethyl)phenyl]-4-piperidinyl]methyl]carbamate.

A mixture of 0.5 g of the compound obtained in preparation 2.20, 0.23 g of the compound obtained in preparation 3.1, 0.184 g of potassium iodide and 0.3 g of $K_2CO_3$ in 20 ml of acetonitrile is left with stirring at AT overnight. It is concentrated under vacuum, the residue is taken up in water, extracted with AcOEt, the organic phase is dried over $Na_2SO_4$ and the solvent is evaporated under vacuum. The residue is chromatographed on silica gel H, eluting with a DCM/MeOH (100/1 to 100/5; v/v) mixture. This gives 0.6 g of the expected product.

$^1$H NMR: DMSO-$d_6$: δ (ppm): 1.1-1.4: 2s: 9H; 1.6-2.5: unres. comp.: 7H; 2.6-4.15: unres. comp.: 14H; 4.2-4.6: sd: 2H; 7.0: d: 1H; 7.3: d: 1H; 7.5-7.9: unres. comp.: 4H.

B) 1-[4-[(Methylamino)methyl]-4-[3-trifluoromethyl)-phenyl]-1-piperidyl]-2-[4-(1,3-thiazol-2-yl)-1-piperazinyl]-1-ethanone.

A solution of 0.6 g of the compound obtained in the preceding step in 20 ml of MeOH is admixed with 20 ml of 2 N hydrochloric ether solution and left with stirring at AT for 3 hours. It is concentrated under vacuum, the residue is taken up with 10% NaOH solution and extracted with DCM, the organic phase is dried over $Na_2SO_4$ and the solvent is evaporated under vacuum. The residue is chromatographed on silica gel H, eluting with a DCM/MeOH (100/1; v/v) mixture. This gives 0.4 g of the expected product.

$^1$H NMR: DMSO-$d_6$+TFA: δ (ppm): 1.8-2.5: unres. comp.: 4H; 3.0-4.1: unres. comp.: 17H; 4.2-4.6: sd: 2H; 6.9: d: 1H; 7.1: d: 1H; 7.6-7.8: unres. comp.: 4H.

The table below illustrates the chemical structures and physical properties of some examples of compounds according to the invention.

In this table
  the value $R_3$=double bond indicates that $R_3$, together with the adjacent carbon atom of the piperidine ring, forms a double bond, as illustrated in Example 2;
  Me, Et, n-Pr, i-Pr, n-Bu, i-Bu, n-Pe and i-Pe represent, respectively, the groups methyl, ethyl, n-propyl, isopropyl, n-butyl, isobutyl, n-pentyl and isopentyl.

TABLE I (I)

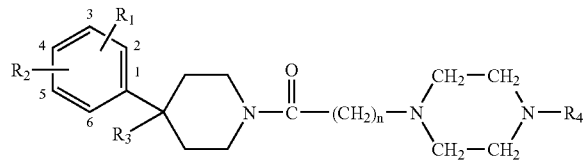

| Compounds No. | n | $R_1$ | $R_2$ | $R_3$ | $R_4$ | m.p. ° C.; salt recrystallization solvent; MH$^+$ |
|---|---|---|---|---|---|---|
| 1 | 1 | 3-$CF_3$ | H | —OH |  | 157-158 DCM/iso ether |
| 2 | 1 | 3-$CF_3$ | H | Double bond |  | 132-133; ether dioxalate |

TABLE I-continued

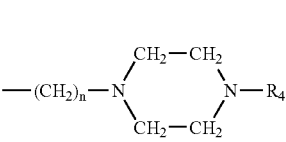

(I)

| Compounds No. | n | $R_1$ | $R_2$ | $R_3$ | $R_4$ | m.p. ° C.; salt recrystallization solvent; MH+ |
|---|---|---|---|---|---|---|
| 3 | 1 | 3-$CF_3$ | H | —$CH_2NH_2$ |  | 3HCl; >232<br>acetone<br>468.4 |
| 4 (a) | 1 | 3-$CF_3$ | 4-Cl | —OH | 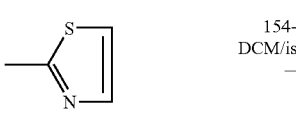 | 186-187<br>DCM/MeOH<br>489.2 |
| 5 (b) | 1 | 3-$OCH_3$ | H | —OH |  | 154-155<br>DCM/iso ether<br>— |
| 6 (c) | 1 | 3-$CH_3$ | H | —OH | 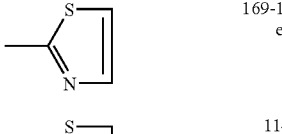 | 147-149<br>DCM/iso ether<br>— |
| 7 (d) | 1 | 3-$CF_3$ | H | —Ome |  | 169-185; HCl<br>ether<br>— |
| 8 (e) | 1 | 3-$OCF_3$ | H | —OH |  | 114-116<br>heptane/iso ether<br>— |
| 9 | 1 | 3-$CF_3$ | H | —$CH_2Nme_2$ | 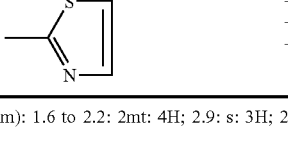 | —<br>—<br>— |
| 10 | 1 | 3-$CF_3$ | H | —$CH_2NHMe$ | | —<br>—<br>— |

$^1$H NMR Spectrum of compound No. 7: DMSO-$d_6$: δ (ppm): 1.6 to 2.2: 2mt: 4H; 2.9: s: 3H; 2.9 to 4.7: m: 14H; 7.0: d: 1H; 7.3: d: 1H; 7.5 to 7.9: m: 4H.
(a) Compound prepared by the procedure described in Example 1, from the compound obtained in preparation 2.17 and the corresponding compound of formula (III).
(b) Compound prepared by the procedure described in Example 1, from the compound obtained in preparation 2.16 and the corresponding compound of formula (III).
(c) Compound prepared by the procedure described in Example 1, from the compound obtained in preparation 2.15 and the corresponding compound of formula (III).
(d) Compound prepared by the procedure described in Example 1, from the compound obtained in preparation 2.4 and the corresponding compound of formula (III).
(e) Compound prepared by the procedure described in Example 1, from the compound obtained in preparation 2.19 and the corresponding compound of formula (III).

The compounds according to the invention were subjected to biochemical studies.

Cell Culture:

The SH—SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM), anti-PPLO (5 ml) (antimycoplasma agent: Tylocine® prepared in a normal saline solution, 6 000 μg/ml), gentamycin (0.1 mg/ml) and glutamine (4 mM) in collagen-coated culture flasks (Becton Dickinson, France).

The stock strain SK-N-BE (human neuroblastoma) and the clone Bep 75 expressing the human $p75^{NTR}$ receptor (SK-N-BE Bep 75) are conventionally cultured in a DMEM culture medium containing FCS (5%), sodium pyruvate (1 mM), anti-PPLO (5 ml), gentamycin (0.1 mg/ml) and glutamine (4 mM).

Study of the Binding of $^{125}$I-NGF to the p75$^{NTR}$ Receptor

The study of the binding of $^{125}$I-NGF (neuronal growth factor radiolabelled with iodine-125) is carried out on a cellular suspension of the two strains SH—SY-5Y and SK-N-BE Bep 75 in accordance with the method described by Weskamp (Neuron, 1991, 6, 649-663). Nonspecific binding is determined by measuring the total binding after one hour of preincubation with the cells at 37° C. in the presence of nonradiolabelled NGF (1 µM). The specific binding is calculated by the difference between the measurement of total binding and the measurement of nonspecific binding. The competition experiments are carried out using a $^{125}$I-NGF concentration of 0.3 nM. The concentrations inhibiting by 50% (IC$_{50}$) the binding of $^{125}$I-NGF to the p75$^{NTR}$ receptor of the compounds according to the invention are low and vary from $10^{-6}$ to $10^{-11}$ M.

Measurement of Apoptosis:

The cells (human neuroblastoma strains SH—SY-5Y and SK-N-BE Bep 75) are established in Petri dishes 35 mm in diameter (Biocoat collagen I) ($10^5$ cells/well) in a DMEM culture medium containing 5% FCS for 24 h. The culture medium is then removed, the cells are rinsed with PBS (Dulbecco's phosphate buffered saline) and either fresh medium containing 5% FCS or medium containing NGF at the concentration of 10 ng/ml is added in the presence or absence of the compounds according to the invention. The levels of apoptosis are measured 48 hours after the treatments in the case of the strain SH—SY-5Y and 24 hours later in the case of the strain SK-N-BE Bep 75 by quantifying the cytoplasmic histones associated with the DNA fragments (cell death detection ELISA, Boehringer Mannheim, Germany). The levels of apoptosis are expressed as quantity of oligonucleosomes/105 cells±SD. Each value corresponds to the mean of 9 experimental points distributed over 3 independent experiments. The compounds of formula (I) exhibit NGF-induced apoptosis inhibitory activity with IC$_{50}$ values varying from $10^{-6}$ to $10^{-11}$ M.

Thus the binding of the compounds according to the invention to the p75$^{NTR}$ receptor results, on the one hand, at the biochemical level, in the inhibition of the dimerization of the receptor induced by neurotrophins, and, on the other hand, at the cellular level, in the inhibition of the proapoptotic effect mediated by the p75$^{NTR}$ receptor.

The compounds according to the invention can therefore be used for the preparation of medicaments, in particular of medicaments intended for the prevention or treatment of any pathology where the p75$^{NTR}$ receptor is involved.

Thus, in another of its aspects, the invention provides medicaments comprising a compound of formula (I), or an addition salt thereof with a pharmaceutically acceptable acid, or alternatively a solvate or a hydrate of the compound of formula (I).

Thus the compounds according to the invention may be used, in humans or in animals, in the treatment or prevention of various p75$^{NTR}$-dependent conditions such as central and peripheral neurodegenerative diseases such as senile dementia, epilepsy, Alzheimer's disease, Parkinson's disease, Huntington's chorea, Down's syndrome, prion diseases, amnesia, schizophrenia; amyotrophic lateral sclerosis, multiple sclerosis; cardiovascular conditions such as post-ischaemic cardiac damage, cardiomyopathies, myocardial infarction, cardiac insufficiency, cardiac ischaemia, cerebral infarction; peripheral neuropathies (of diabetic, traumatic or iatrogenic origin); damage to the optic nerve and to the retina; spinal cord trauma and cranial trauma; atherosclerosis; stenoses; cicatrization; alopecia.

The compounds according to the invention may also be used in the treatment of cancers such as that of the lung, of the thyroid, of the pancreas, of the prostate, of the small intestine and of the colon, of the breast, in the treatment of tumours, of metastases and of leukaemias.

The compounds according to the invention may also be used in the treatment of chronic neuropathic and inflammatory pain and in the treatment of autoimmune diseases such as rheumatoid arthritis.

The compounds according to the invention may also be used in the treatment of bone fractures and in the treatment or prevention of bone diseases such as osteoporosis.

In another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and at least one pharmaceutically acceptable excipient.

The said excipients are selected, according to the pharmaceutical form and the desired mode of administration, from the customary excipients which are known to the person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, solvate or hydrate where appropriate, may be administered in unit form for administration, as a mixture with conventional pharmaceutical excipients, to animals and to human beings for the prophylaxis or treatment of the above disorders or diseases.

The appropriate unit forms for administration comprise the forms for oral administration such as tablets, soft or hard gelatin capsules, powders, granules and oral solutions or suspensions, forms for sublingual, buccal, intratracheal, intraocular or intranasal administration, forms for administration by inhalation, forms for topical, transdermal, subcutaneous, intramuscular or intravenous administration, forms for rectal administration and implants. For topical application, the compounds according to the invention may be used in creams, gels, ointments or lotions.

By way of example, a unit form for administration of a compound according to the invention in tablet form may comprise the following components:

| | |
|---|---:|
| Compound of the invention | 50.0 mg |
| Mannitol | 223.75 mg |
| Croscaramellose sodium | 6.0 mg |
| Cornstarch | 15.0 mg |
| Hydroxypropylmethylcellulose | 2.25 mg |
| Magnesium stearate | 3.0 mg |

For oral administration, the dose of active principle administered per day may be up to 0.01 to 100 mg/kg, in single or divided doses, preferably 0.02 to 50 mg/kg.

There may be particular cases in which higher or lower dosages are appropriate; such dosages are not outside the scope of the invention. According to the customary practice, the dosage appropriate for each patient is determined by the doctor according to the mode of administration, the weight and the response of the said patient.

The present invention, in another of its aspects, also relates to a method of treating the pathologies indicated above which comprises the administration, to a patient, of an effective dose of a compound according to the invention, or one of its pharmaceutically acceptable salts or its hydrates or solvates.

The invention claimed is:

1. A compound of formula (I):

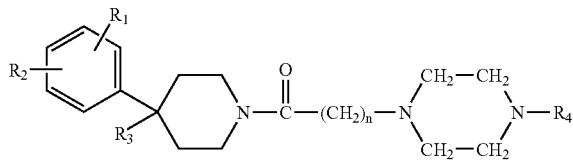

in which:
n is 1 or 2;
$R_1$ represents a halogen atom; a trifluoromethyl radical; a $(C_1-C_4)$alkyl; a $(C_1-C_4)$alkoxy; or a trifluoromethoxy radical;
$R_2$ represents a hydrogen atom or a halogen atom;
$R_3$ represents a hydrogen atom; a group —$OR_5$; a group —$CH_2OR_5$; a group —$NR_6R_7$; a group —$NR_8COR_9$; a group —$NR_8CONR_{10}R_{11}$; a group —$CH_2NR_{12}R_{13}$; a group —$CH_2NR_8CONR_{14}R_{15}$; a $(C_1-C_4)$alkoxycarbonyl; or a group —$CONR_{16}R_{17}$;
or else $R_3$ constitutes a double bond between the carbon atom to which it is attached and the adjacent carbon atom of the piperidine ring;
$R_4$ represents the aromatic group 1,3-thiazol-2-yl of formula:

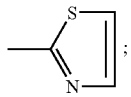

$R_5$ represents a hydrogen atom; a $(C_1-C_4)$alkyl; or a $(C_1-C_4)$alkylcarbonyl;
$R_6$ and $R_7$ represent each independently a hydrogen atom or a $(C_1-C_4)$alkyl;
$R_8$ represents a hydrogen atom or a $(C_1-C_4)$alkyl;
$R_9$ represents a $(C_1-C_4)$alkyl or a group —$(CH_2)_m$—$NR_6R_7$;
m is 1, 2 or 3;
$R_{10}$ and $R_{11}$ represent each independently a hydrogen atom or a $(C_1-C_4)$alkyl;
$R_{12}$ represents a hydrogen atom or a $(C_1-C_5)$alkyl;
$R_{13}$ represents a hydrogen atom, a $(C_1-C_5)$alkyl, a group —$(CH_2)_q$—OH or a group —$(CH_2)_q$—S—$CH_3$;
or else $R_{12}$ and $R_{13}$, together with the nitrogen atom to which they are attached, constitute a heterocycle selected from aziridine, azetidine, pyrrolidine, piperidine and morpholine;
q is 2 or 3;
$R_{14}$ and $R_{15}$ represent each independently a hydrogen atom or a $(C_1-C_4)$alkyl;
$R_{16}$ represents a hydrogen atom or a $(C_1-C_4)$alkyl;
$R_{17}$ represents a hydrogen atom, a $(C_1-C_4)$alkyl or a group $(CH_2)_q$—$NR_6R_7$;
or else $R_{16}$ and $R_{17}$, together with the nitrogen atom to which they are attached, constitute a heterocycle selected from azetidine, pyrrolidine, piperidine, morpholine and piperazine which is unsubstituted or substituted in position 4 by a $(C_1-C_4)$alkyl;
or an acid addition salt hydrate or solvate thereof.

2. A compound according to claim 1 wherein:
n is 1;
$R_1$ is in position 3 of the phenyl and represents a trifluoromethyl radical, a methyl, a methoxy or a trifluoromethoxy radical and $R_2$ represents a hydrogen atom; or else $R_1$ is in position 3 of the phenyl and represents a trifluoromethyl radical and $R_2$ is in position 4 of the phenyl and represents a chlorine atom; and
$R_3$ represents a hydroxyl, a methoxy, an aminomethyl, a (methylamino)methyl, or a (dimethylamino)methyl; or else $R_3$ constitutes a double bond between the carbon atom to which it is attached and the adjacent carbon atom of the piperidine ring;
$R_4$ represents a 1,3-thiazol-2-yl.

3. A process for preparing a compound according to claim 1
wherein a compound of formula (IIa)

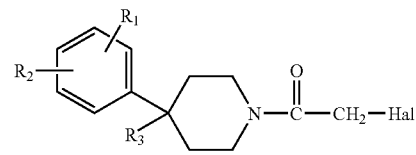

in which $R_1$, $R_2$ and $R_3$ are as defined in claim 1 and Hal represents a halogen atom is reacted with a compound of formula (III)

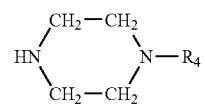

in which $R_4$ is as defined in claim 1.

4. A process for preparing a compound according to claim 1 in which n=2
wherein a compound of formula (IIb)

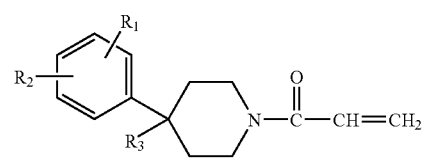

in which $R_1$, $R_2$ and $R_3$ are as defined in claim 1 is reacted with a compound of formula (III)

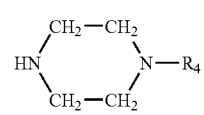

in which $R_4$ is as defined in claim 1.

5. A process for preparing a compound according to claim 1 in which $R_3$ represents a group —$CH_2NR_{12}R_{13}$ in which $R_{12}$ and $R_{13}$ each represent hydrogen wherein a compound of formula (IIc) or (IId)

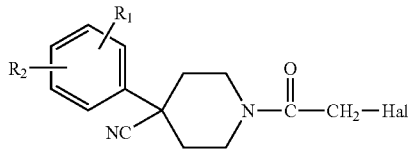 (IIc)

or

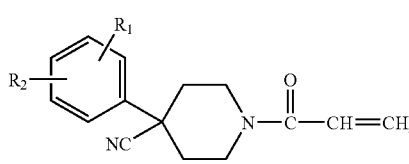 (IId)

in which R₁ and R₂ are as defined in claim 1 and Hal represents a halogen atom, is reacted with a compound of formula (III)

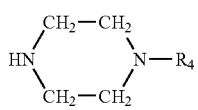 (III)

in which R₄ is as defined in claim 1 to give a compound of formula (Ia)

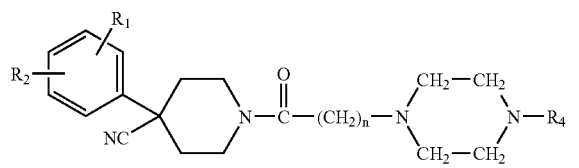 (Ia)

and the cyano group of the compound of formula (Ia) is reduced.

6. A compound of formula

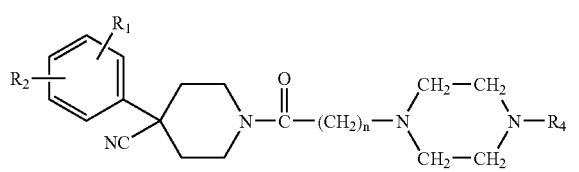 (Ia)

in which:
n is 1 or 2;
R₁ represents a halogen atom; a trifluoromethyl radical; a (C₁-C₄)alkyl; a (C₁-C₄)alkoxy; or a trifluoromethoxy radical;
R₂ represents a hydrogen atom or a halogen atom; and
R₄ represents the aromatic group 1,3-thiazol-2-yl of formula:

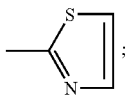

or an acid addition salt thereof.

7. A compound according to claim 1 selected from the group consisting of:
1-[4-hydroxy-4-[3-(trifluoromethyl)phenyl]-1-piperidyl]-2-[4-(1,3-thiazol-2-yl)-1-piperazinyl]-1-ethanone;
2-[4-(1,3-thiazol-2-yl)-1-piperazinyl]-1-[4-[3-(trifluoromethyl)phenyl]-3,6-dihydro-1-(2H)-pyridinyl]-1-ethanone;
1-[4-(aminomethyl)-4-[3-(trifluoromethyl)phenyl]-1-piperidyl]-2-[4-(1,3-thiazol-2-yl)-1-piperazinyl]-1-ethanone;
1-[4-[4-chloro-3-(trifluoromethyl)phenyl]-4-hydroxy-1-piperidyl]-2-[4-(1,3-thiazol-2-yl)-1-piperazinyl]-1-ethanone;
1-[4-hydroxy-4-(3-methoxyphenyl)-1-piperidyl]-2-[4-(1,3-thiazol-2-yl)-1-piperazinyl]-1-ethanone;
1-[4-hydroxy-4-(3-methylphenyl-1-piperidyl]-2-[4-(1,3-thiazol-2-yl)-1-piperazinyl]-1-ethanone;
1-[4-methoxy-4-[3-(trifluoromethyl)phenyl]-1-piperidyl]-2-[4-(1,3,-thiazol-2-yl)-1-piperazinyl]-1-ethanone;
1-[4-hydroxy-4-[3-(trifluoromethoxy)phenyl]-1-piperidyl]-2-[4-(1,3-thiazol-2-yl)-1-piperazinyl]-1-ethanone;
1-[4-[(dimethylamino)methyl]-4-[3-(trifluoromethyl)phenyl]-1-piperidyl]-2-[4-(1,3-thiazol-2-yl)-1-piperazinyl]-1-ethanone;
1-[4-[(methylamino)methyl]-4-[3-(trifluoromethyl)phenyl]-1-piperidyl]-2-[4-(1,3-thiazol-2-yl)-1-piperazinyl]-1-ethanone;
or an acid addition salt thereof.

8. A pharmaceutical composition comprising a compound according to claim 1 together with a pharmaceutically acceptable excipient.

9. A pharmaceutical composition comprising a compound according to claim 2 together with a pharmaceutically acceptable excipient.

10. A pharmaceutical composition comprising a compound according to claim 7 together with a pharmaceutically acceptable excipient.

* * * * *